(12) United States Patent
Taylor et al.

(10) Patent No.: US 6,547,821 B1
(45) Date of Patent: Apr. 15, 2003

(54) SURGICAL PROCEDURES AND DEVICES FOR INCREASING CARDIAC OUTPUT OF THE HEART

(75) Inventors: Charles S. Taylor, San Francisco; Michael V. Morejohn, San Jose, both of CA (US)

(73) Assignee: Cardiothoracic Systems, Inc., Santa Clara, CA (US)

( * ) Notice: Subject to any disclaimer, the term of this patent is extended or adjusted under 35 U.S.C. 154(b) by 0 days.

(21) Appl. No.: 09/116,362

(22) Filed: Jul. 16, 1998

(51) Int. Cl.[7] .......................... A61M 1/10; A61N 1/362
(52) U.S. Cl. ........................... 623/3.1; 600/16
(58) Field of Search .................. 600/16, 17, 18, 600/37; 623/3.1; 128/898

(56) References Cited

U.S. PATENT DOCUMENTS

| | | | |
|---|---|---|---|
| 3,053,249 A | 9/1962 | Smith | 128/39 |
| 3,513,836 A | 5/1970 | Sausse | 128/64 |
| 4,048,987 A | 9/1977 | Hurson | 128/20 |
| 4,690,134 A | 9/1987 | Snyders | 128/64 |
| 4,726,356 A | 2/1988 | Santilli et al. | 128/20 |
| 4,852,552 A | 8/1989 | Chaux | 128/20 |
| 4,957,477 A | 9/1990 | Lundback | 600/16 |
| 5,131,905 A | 7/1992 | Grooters | 600/16 |
| 5,150,706 A | 9/1992 | Cox et al. | 128/400 |
| 5,167,223 A | 12/1992 | Koros et al. | 128/20 |
| 5,256,132 A | * 10/1993 | Snyders | |
| 5,509,890 A | 4/1996 | Kazama | 600/37 |
| 5,702,343 A | 12/1997 | Alferness | 600/37 |
| 5,713,954 A | 2/1998 | Rosenberg et al. | 623/3 |
| 5,800,528 A | 9/1998 | Lederman et al. | 623/3 |

* cited by examiner

*Primary Examiner*—Bruce Snow
(74) *Attorney, Agent, or Firm*—Thelen Reid & Priest LLP

(57) ABSTRACT

Methods and devices for passively assisting the cardiac function of the heart are disclosed. A method of increasing the cardiac output of a heart includes providing a site of surgical access to the portion of the heart to be restrained, reducing the cardiac expansion of the portion of the heart to be restrained, and maintaining the reduction of cardiac expansion of the portion of the heart to be restrained for a substantial amount of time. Cardiac assist devices for increasing the cardiac output of the heart are disclosed comprising a reinforcing portion configured to contact a portion of the heart tissue wherein the reinforcing portion restricts the expansion of the portion of the heart tissue. The reinforcing portion can be a number of structures, including pads, frames, straps, and other retaining means for limiting cardiac expansion of the portion of the heart tissue to be restrained.

12 Claims, 16 Drawing Sheets

SURGICAL PROCEDURES AND DEVICES FOR INCREASING CARDIAC OUTPUT OF THE HEART

Diseases of the cardiovascular system affect millions of people each year and are a leading cause of death in the United States and throughout the world. The costs to society from such diseases is enormous both in terms of the lives lost and in terms of the cost of treating patients through surgery. A particularly deadly form of heart disease which afflicts an estimated 3 million Americans is Congestive Heart Failure (CHF). Congestive heart failure is a syndrome caused by a failing heart, with congestion in the pulmonary or systemic circulation or both. It afflicts males more often than females, blacks more often than whites, and the elderly more often than younger persons. It is one of the most frequent causes of hospitalization of people aged 65 and older. Despite improvements in the management of patients with CHF, there appears to be no decline in mortality, presumably because of the aging of the population and the improved survival of patients with predisposing conditions, such as chronic ischemic heart disease.

The most common cause of congestive failure is coronary artery disease—narrowing of the arteries supplying blood to the heart muscle. Although coronary disease often starts at an early age, congestive failure occurs most often in the elderly. Among people more than 70 years old, about 8 out of 1,000 are diagnosed with congestive heart failure each year. The majority of these patients are women, probably because men are more likely to die from coronary artery disease before it progresses to heart failure.

Heart failure is also associated with untreated hypertension, alcohol abuse, and drug abuse (primarily cocaine and amphetamines) at any age. Hyperthyroidism and various abnormalities of the heart valves (particularly aortic and mitral) are among the other disorders that can cause heart failure. In addition, viral infection or inflammation of the heart (myocarditis) or primary heart muscle disease (cardiomyopathy), and in rare instances, extreme vitamin deficiencies, can result in heart failure.

Heart failure may occur suddenly, or it may develop gradually. When heart function deteriorates over years, one or more conditions may exist. The strength of muscle contractions may be reduced, and the ability of the heart chambers to fill with blood may be limited by mechanical problems, resulting in less blood to pump out to tissues in the body. Conversely, the pumping chambers may enlarge and fill with too much blood when the heart muscle is not strong enough to pump out all the blood it receives. In addition, as the architecture of the heart changes as it enlarges, regurgitation of the mitral valve may develop, making the heart failure even worse. An enlarged heart, called cardiomyopathy, is a particularly debilitating form of heart disease which effects as many as 40% of patients with congestive heart failure.

Traditional therapeutic techniques for the treatment of congestive heart failure have been less than completely effective for a majority of patients treated. Drug therapy is one of the most widely used means of reducing the debilitating effects of CHF and for improving the quality of life of patients. Diuretics are often prescribed to help the kidneys eliminate excess water and sodium, thereby reducing the blood volume and the heart's workload. Digitalis may be prescribed to increase the heart's pumping action and increase the work done by the heart. Vasodilators, including angiotensin converting enzyme (ACE) inhibitors, may be used, along with diuretics, in patients with mild-to-moderate or severe congestive failure. ACE inhibitors, which include captopril (Capoten) and enalapril (Vasotec), block the production of a substance called angiotensin II, a potent constrictor of blood vessels. By causing the dilation of blood vessels, vasodilators decrease the amount of work that must be done by the heart as the blood pressure of the patient is decreased with increased vessel diameter. Nitrates and glycosides are also widely utilized in the treatment of heart failure to improve cardiac function and decrease symptoms.

Drug therapy has proved to be ineffective in completely treating more severe forms of CHF. Although ACE inhibitors and newer drug combinations have provided some relief for many patients, drugs often do not attack the root of the problem: a weak heart. Although workload on the heart is decreased through drug therapy, the pumping action of the heart is generally not improved long term in the case of most drugs. Also, in the case of drugs like digitalis, nitrates and glycosides, researchers remain unsure as to the long term debilitating affects that these drugs may have on an already weakened heart. Many believe that enhancement of the heart's performance through drug therapy further damages the weakened muscles of the heart in the long term. Drug therapy may also be less than desirable for patients who suffer from moderate to severe side effects. For example, the use of ACE inhibitors often is accompanied by a persistent cough. Angioedema is another potential side effect of ACE inhibitors which can be potentially life threatening. Diuretics may dangerously decrease the body's supply of potassium and other important vitamins and require additional corrective measures to maintain proper body chemistry. Finally, drug therapy often results in only short term gains to the patient. Although short term mortality of patients may be reduced in patients using aggressive drug therapy, after 3 to 5 years, drugs often offer little reduction in the rate of mortality for CHF patients.

Surgical intervention is another means for improving the condition of weakened hearts. When heart failure is due to valvular disease, the patient may have surgical implantation of an artificial heart valve or valve repair to help increase cardiac function. Surgery may also be helpful in correcting congenital heart defects that can lead to heart failure. Coronary artery bypass graft surgery or catheterization using balloon angioplasty are among the therapeutic techniques used to prevent and treat heart failure caused by occluded, or blocked, arteries. Additionally, newer techniques for myocardial revascularization and improved cardiac functioning include transmyocardial laser revascularization, implantation of mechanical assist devices, implantable cardioverters/defibrillators and dynamic cardiomyoplasty.

Implantation of permanent or temporary mechanical assist devices is one method by which ventricular function can be augmented in a diseased heart. A number of devices and methods are known in the art for compensating mechanically for the reduced ventricular output. Such devices include rotary blood flow pumps, intraaortic balloon pumps, axial flow pumps, external mechanical assist devices, and centrifugal blood flow pumps. The pump devices are traditionally used to augment the functioning of the left or right side of the heart by removing blood from one portion of the heart into a downstream portion of the patient's vasculature. For example, for ventricular "unloading" of the left heart, an axial flow pump may be inserted into the left ventricle via the aortic arch of the patient. The pump will remove blood from the ventricle and pump it into the aortic arch where it will flow normally to the remainder of the patient's arterial system. Right heart unloading is similarly accomplished except that blood is typically removed from the right atrium or ventricle and pumped into the pulmonary artery. In contrast, external ventricular assist devices are generally surgically attached to the external surface of the heart and compress the ventricle of the heart during contraction so as to augment the contraction and improve cardiac output.

Mechanically assisting the functioning of the heart often presents substantial practical problems which prevent this method of CHF treatment from being the most desirable therapeutic option. Mechanical assist devices are often very expensive and difficult to install. Devices which have components external to the patient can detract significantly from the quality of life of the patient. Installation of the device may also lead to infection or rejection of the device by the patient's immune system. Thrombosis is also a potential complication caused by foreign bodies within the patient's bloodstream. The potential for thrombosis often requires aggressive anticoagulant therapy to prevent embolic material from forming in the bloodstream and causing serious physiological consequences. Mortality is also still high in those patients who have a cardiac assist device installed. Because of the high incidence of complications with cardiac assist devices, patients are often weaned from the device after the heart has been given a chance to rest and recover during a period of ventricular unloading. The hope is that the ventricular output will improve to a point that the patient may function without the device. Cardiac assist devices may also be used as a bridge to cardiac transplantation to support a patient with a failed heart while a suitable donor heart is being located for the patient.

Cardiac transplantation is another technique for treating heart disease. Cardiac transplantation is usually viewed as the last option for a patient with end-stage (terminal) heart disease. Unfortunately, for most patients suffering from congestive heart failure, cardiac transplantation may be the only currently available therapeutic option. As the name suggests, cardiac transplantation is a procedure wherein a healthy heart is taken from a donor cadaver and used to replace the diseased heart of the patient. Transplantation is accompanied by many risk factors which contribute to a high incidence of failed procedures and undesirability as a therapeutic option. These risk factors include the age of the patients, a decreasing number of donors, the extremely high cost of the procedure, high mortality on the waiting list, high morbidity under immunosuppressive therapy and problems with graft vasculopathy. Because of the high mortality of the procedure, cardiac transplantation is considered a last resort for treating CHF.

Spurred by the complications associated with existing therapeutic options for treating dilated cardiomyopathy (an enlarged heart), surgeons have experimented with a method by which the ventricle of the heart is reduced in size to more approximate the heart's normal architecture. Called ventricular remodeling, the procedure requires the surgeon to remove a golf-ball size piece of tissue from the ventricle wall and then reshape the heart into a more efficient pumping machine. The procedure is usually accompanied by repair or replacement of any leaky or malfunctioning heart valves and those damaged or destroyed by the remodeling itself. One of the complications of dilated cardiomyopathy is that a considerable amount of "dead space" exists within the enlarged ventricle which is not expelled during the contraction of the weakened heart, thus reducing the efficiency of the heart. Ventricular remodeling reduces the size of the diseased ventricle and eliminates the "dead space" within the ventricle, resulting in an overall increase in the efficiency of the heart.

Due to the high incidence of complications of ventricular remodeling, it is not always the most desirable means of treating CHF. The procedure fails in approximately 1 in 4 patients undergoing the procedure. These patients must then be supported by a mechanical support device as described above or must undergo an immediate heart transplant procedure to survive. The procedure is also only effective for correcting decreased cardiac functioning resulting from dilated cardiomyopathy. Approximately 60% of CHF patients who are in need of a heart transplant to survive do not have an enlarged heart and would not be aided by the procedure.

From the foregoing it can be seen that CHF is a particularly deadly disease which affects millions of Americans every year. Traditional therapeutic techniques have also proven less than completely effective with most forms of CHF. Drug therapies, implantable devices, and currently known surgical procedures have a number of associated complications and risks which can prove potentially deadly to the patient.

Thus, it would be desirable to have devices and techniques which increase the cardiac output of a diseased heart without the associated complications and risks of known devices and techniques. Such devices should be simply and easily installed with a minimum of trauma to the patient, and preferably, would be capable of installation using minimally invasive surgical techniques. Use of the device should also be possible without the need to put the patient through the trauma of a "stopped heart" operation supported by cardiopulmonary bypass. The devices and techniques would preferably be employed as a permanent means of cardiac augmentation or, alternatively, as a temporary means of improving cardiac performance while awaiting a heart transplant.

SUMMARY OF THE INVENTION

A preferred device of the present invention comprises a ventricular assist device for increasing the ventricular output of the heart without providing external mechanical assistance to the heart, the device comprising a reinforcing portion operably engaging a portion of the heart tissue wherein the reinforcing portion is configured to restrict the motion of the portion of the heart tissue. The reinforcing portion is configured so that the heart tissue is prevented from expanding fully where the tissue is engaged by the reinforcing portion. A number of means exist for creating the reinforcing portion of the device. In one preferred embodiment, the reinforcing portion comprises a plurality of pursestring sutures installed in the portion of the heart tissue to be restricted, wherein the placement of the pursestring sutures defines the portion of the heart tissue to be restrained.

In another embodiment, the reinforcing portion comprises a patch of material installed in facing engagement to the portion of the heart tissue to be restrained. A number of materials are suitable for this application, including nylon, plastic, silicone, stainless steel, polyester fabric, pericardial tissue (either human, bovine, or porcine tissue), and other biocompatible biologic material. The material may be fixed in facing engagement to the portion of the heart tissue to be restrained using a plurality of sutures. Staples, tissue adhesive, rivets, and other standard surgical fastening techniques may also be used to fix the reinforcing material to the surface of the heart.

In another embodiment of the device of the present invention, the reinforcing portion comprises a pad assembly engaging the portion of heart to be restrained. The pad assembly is preferably configured to reduce the ventricular expansion of the portion of the heart to be restrained. The pad assembly may be held in engagement with the surface of the heart by a frame made from a number of members which encircle the heart and hold the pad assembly firmly against the portion of the heart to be restrained. The pad assembly may also be held in place by a harness made from highly flexible straps of biocompatible material, wherein the harness encircles around the heart to hold the pad assembly firmly against the portion of the heart tissue to be restrained.

In another embodiment of the present invention, the pad assembly is held in engagement with the portion of the heart tissue to be restrained with an anchor member. The anchor member is preferably stainless steel or other biocompatible material such as polypropylene or nylon, which is fastened at one end to the surface of the heart to be restrained. The second end of the anchor member is configured to be anchored to a relatively fixed structure in relation to the portion of the heart to be restrained. In one embodiment of the device of the present invention, the second end of the anchor member is configured to be fixed to a rib of a patient. Alternatively, the sternum bone or other suitable skeletal structure may be used to fix the motion of the portion of the heart to be restrained. It is only important that the portion of the heart to be restrained be fixed in relation to the remainder of the heart during expansion of the heart. In one embodiment of the present invention, the second end of the anchor member is configured to be fixed to a wall of the heart opposite the portion of the heart to be restrained. The anchor portion is thus installed inside the ventricle or atrium of the heart and restrains a portion of the heart wall by fixing the portion of the heart to be restrained to an opposite wall of the heart, such as a septal wall.

In a preferred embodiment, the reinforcing portion comprises an annular ring engaging the portion of the heart to be restrained. The ring may be sewn to the portion of the heart to be restrained, or it may be fixed using staples, surgical adhesive, or other traditional surgical fastening methods, or it may be held in engagement with the portion of the heart to be restrained using a harness or frame made from flexible straps or members as previously described.

In another embodiment of the present invention, the reinforcing portion comprises two or more motion restricting pads which are sutured, stapled, or otherwise fastened to the surface of the heart and then conjoined using one or more straps or tethers. The straps may be adjusted to pull the pads closer in relation to each other and thus reduce the motion of the heart wall between the two or more reinforcing pads.

The methods of the present invention for passively assisting cardiac performance generally comprise the steps of (1) providing a site of surgical access to the portion of the heart to be restrained; and (2) reducing the ventricular movement of the portion of the heart to be restrained. In one method of the present method, the step of reducing the ventricular movement of the portion of the heart to be restrained comprises installing a plurality of sutures in the portion of the heart to be restrained. In another method, the step of reducing the ventricular movement of the portion of the heart to be restrained comprises installing a patch of reinforcing material in facing engagement with the portion of the heart to be restrained. The patch may be installed using sutures, staples, surgical adhesive, and other surgical fastening techniques. Yet in another method, the step of reducing the ventricular movement of the portion of the heart to be restrained comprises fixing a portion of the pericardium of a patient or from a donor to the portion of the heart to be restrained. In an alternative method of the present invention, the step of reducing the ventricular movement of the portion of the heart to be restrained comprises fixing the portion of the heart to be restrained to a body structure which is relatively fixed in relation to the portion of the heart to be restrained. The body structure may be the patients ribs, sternum, or wall of the heart opposite the portion to be restrained.

Additional steps of the methods of the present invention may include the step of closing the site of surgical access. The method of the present invention may also be practiced on a patient who is supported by cardiopulmonary bypass (CPB) prior to reducing the ventricular movement of the portion of the heart to be restrained. Preferably, however, the methods of the present invention will be practiced in a minimally invasive manner and on a beating heart.

Another embodiment of the present invention is device for displacing a volume of a portion of a diseased heart comprising an expandable member configured to fit into a chamber of the diseased heart and reduce the available blood volume of the chamber of the heart; and an inflation portion. A method of using the volume displacement device of the present invention includes installing a ventricular displacement device comprising an inflation portion and an expandable member into the chamber of the heart, and expanding the expandable member to displace a portion of the blood volume of the chamber of the heart.

Alternatively, the volume of a chamber may be reduced using the teachings of the present invention by making an incision through the pericardium and myocardium of the left ventricle, repairing the incision in the pericardium; pushing the pericardium into the ventricle through the incision in the myocardium to form a pericardial sack in the left ventricle; providing inflation fluid to the pericardial sack to fill the pericardial sack and displace a portion of the blood volume of the ventricle; and closing the incision in the myocardium to close surgical access to the ventricle and to seal the inflation fluid in the pericardial sack.

DETAILED DESCRIPTION OF THE INVENTION

Figure 1:
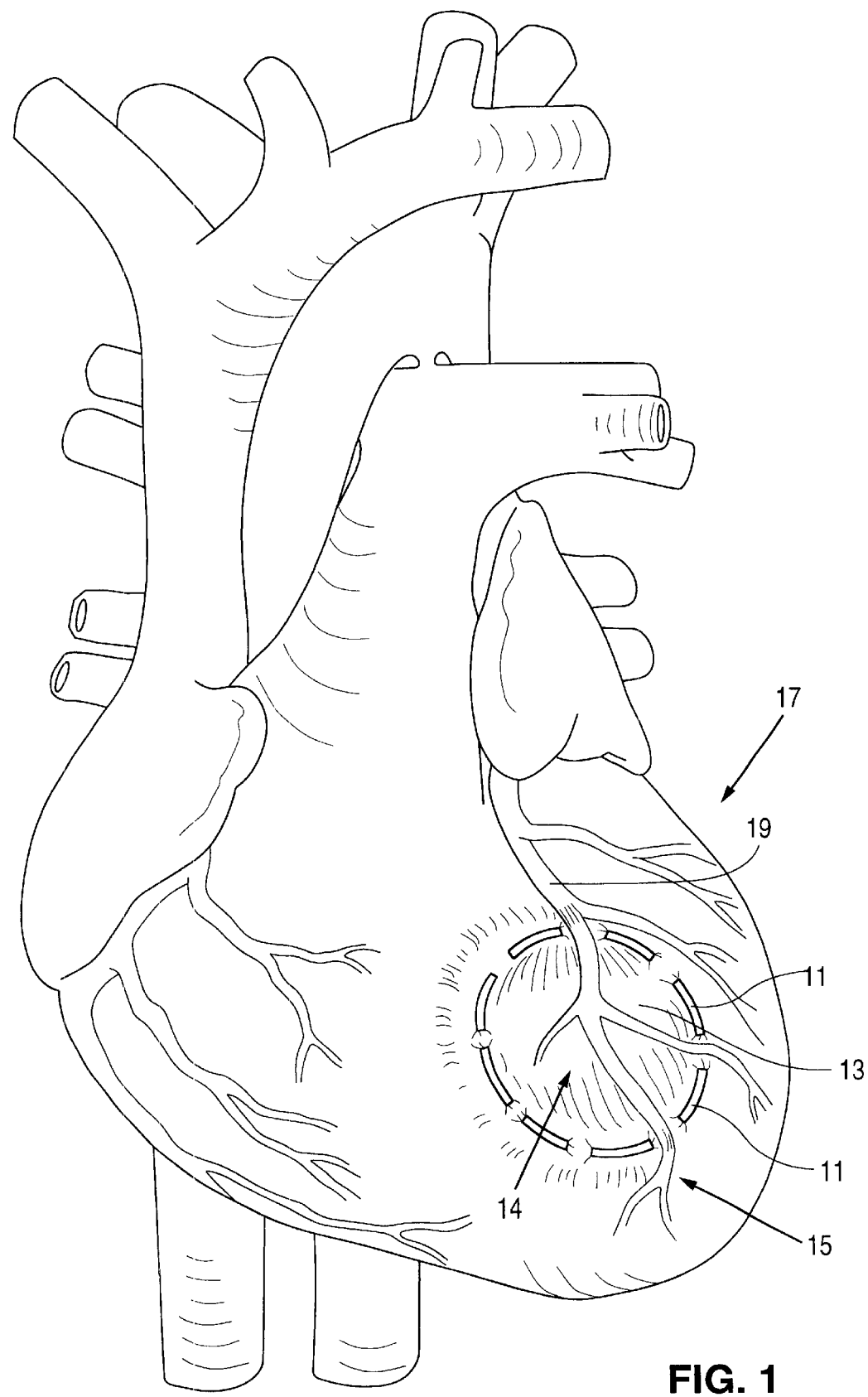
FIG. 1 is a method of passive ventricular assist in accordance with the teachings of the present invention wherein a ring shaped portion of a distended myocardium of a diseased heart is restrained with a series of pursestring sutures.

The devices and methods of the present invention will be described with reference to the attached drawings. By way of illustration and example, the devices and methods of the present invention will be described for use to increase the output of the left ventricle of the heart. However, it is to be understood that the present invention can also be configured to increase right and left atrial functioning of the heart as well as the right ventricular functioning.

It has been found that a localized restriction on the muscle of the heart can increase the blood flow from the heart out the bloodflow tract. A "passive" ventricular assist device constructed in accordance with teachings of the present or a method of "passively" assisting cardiac function augments cardiac function without mechanically assisting the physical contraction or expansion of the heart muscle. Several embodiments of the present invention apply a restriction on the motion of the heart muscle to compensate for the debilitating effects caused by heart disease, coronary artery aneurysms, and other vascular complications by reducing ventricular and atrial blood volume (the volume of the heart chamber occupied by blood during systole and diastole) and increasing the cardiac blood outflow. Other teachings of the present invention comprise methods and devices for reducing cardiac blood volume through altering the internal geometry of one or more chambers of the heart. The teachings of the present invention comprise devices and methods wherein the cardiac expansion and/or the cardiac volume of a heart chamber is limited so as to increase cardiac output without mechanically augmenting the performance of the heart.

A first step in a method to increase cardiac functioning using the devices and methods of the present invention is to provide surgical access to the heart. Access may be provided using any number of approaches, including but not limited to a sternotomy, thoracotomy, or sub-xyphoid approach. Access may also be provided endoscopically through a trocar port or other percutaneous incision in the chest wall or it may be provided in a minimally invasive manner, e.g., using a mini-thoracotomy or mini-sternotomy.

The devices and methods of the present invention are capable of being installed on either a stopped heart which has been placed on cardiopulmonary bypass (CPB), on a partially assisted heart. Generally, for a CPB procedure, the heart and lungs are isolated from the rest of the patient's vascular system while the patient is supported using a heart lung machine which oxygenates the patient's venous blood and provides fresh arterial blood to the patient's arterial system. The heart is then stilled and cooled during the procedure and a protective solution is provided to the heart to prevent ischemia of the heart muscle which may result from the interruption of coronary blood flow.

Beating heart procedures are also well known in the art and are more fully described in copending U.S. patent application Ser. No. 08/752,741, incorporated herein by reference in its entirety. It is often preferable to operate on a beating heart to prevent the potentially fatal complications that often accompany complete stoppage and bypass of the heart. The beating heart may be partially stabilized using a stabilizing means as described in copending U.S. patent application Ser. No. 08/789,751, incorporated herein by reference in its entirety. Stabilization simplifies surgical procedures on the heart and increases the patency and effectiveness of cardiac repairs. The surgeon may take additional measures to restrict the movement of the heart within the chest cavity. For example, an inflatable cushion or straps or laces may be inserted beneath or surrounding the heart. Additionally, when the pericardium is available, the pericardium may be incised and used to position the beating heart. When the pericardium is available, the surgeon can use the pericardium to raise and rotate the beating heart within the chest cavity and maintain the position by suturing the pericardium to the periphery of the access incision.

Cardiac procedures can also be performed on a partially supported heart. For example, an axial flow pump may be installed in the left ventricle in order to unload the ventricle. An unloaded ventricle reduces the size and oxygen consumption of the heart as well as the motion of the heart during contraction. By reducing the size of the heart, the surgeon is better able to operate on the heart, especially for endoscopic or minimally invasive access procedures. Reduced oxygen consumption prevents myocardial ischemia and cardiac "stunning," a condition that often results from temporary deprivation of blood to the heart tissue. Obviously, reduced heart motion improves the patency and effectiveness of surgical procedures performed on the heart. The right or left side of the heart can also be unloaded with other previously described cardiac assist devices which are well known in the art.

Once a surgical access site to the heart has been provided, either on a stilled heart, a beating heart, or a partially assisted beating heart, the surgeon will reinforce, constrict, or constrain at least a portion of the heart muscle so as to limit the expansion of the heart muscle in the reinforcing portion using the devices or methods of the present invention. FIG. 1 shows one method of the present invention wherein a localized reinforcing portion 14 on the surface of the heart 17 is used to create a restriction on the ventricular expansion of the heart 17. The reinforced area 14 is created by installing a number of pursestring sutures 11 in the myocardium in the area desired to be reinforced. The sutures function to stiffen the myocardial surface and prevent free movement of the muscle during systole and diastole. The sutures 11 may be arranged in a ring so as to completely define the reinforcing portion 14 to be restrained. The sutures may also be in an interlacing pattern 11a or be replaced with staples or other fastening devices in order to create the reinforcing portion. The ring of sutures operates to prevent the myocardium from expanding planarly outside the bounds of the ring. Various suture techniques may be used in addition to simple interrupted sutures, including interrupted vertical mattress, interrupted horizontal mattress with or without pledgets, or continuous, depending on the degree of restraint desired and the particular patient anatomy.

Figure 8A:
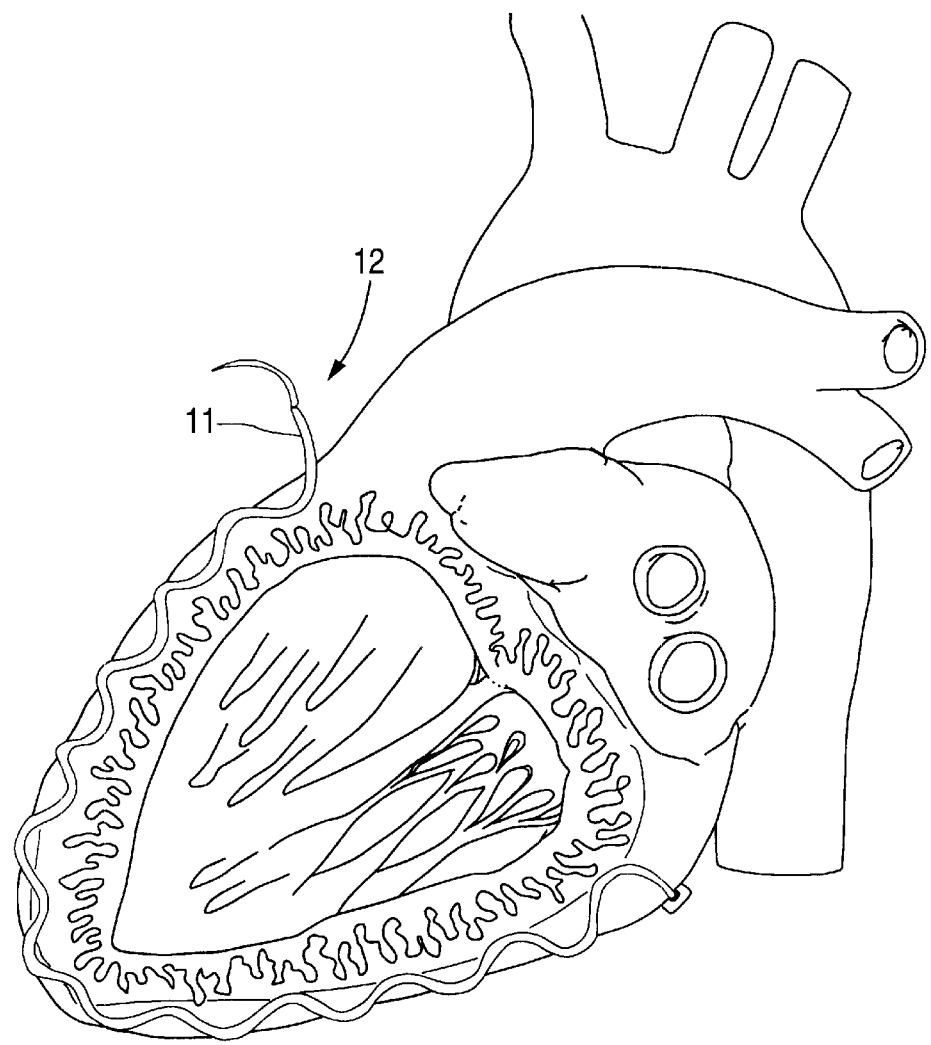
FIG. 8A shows a method of passively assisting cardiac function by installing one of more sutures in the surface of the myocardium, wherein the heart is shown in partial cutaway to show the emplacement of a suture in the heart tissue.
Figure 8B:
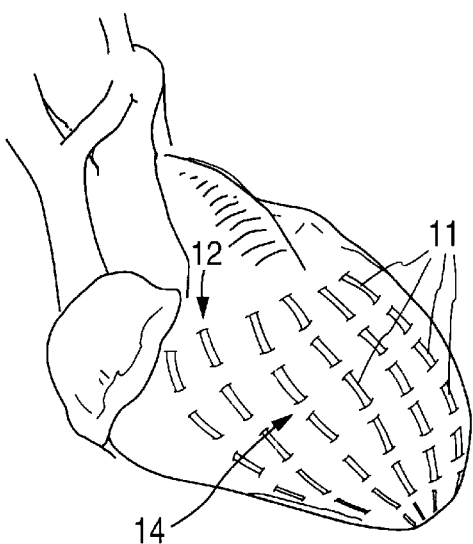
FIG. 8B shows the a plurality of sutures as shown in FIG. 8A configured to form a reinforcing portion on the surface of the heart.

FIGS. 8A and 8B show another embodiment of the present invention wherein one or more sutures 11 are installed in the surface of the myocardium in one or more rows 12 to restrict the motion of the myocardium during expansion of the heart. FIG. 8A shows one possible arrangement for the installation of a suture 11 to form a single row 12 which reinforces the surface of the heart. As shown in FIG. 8B, the rows 12 of sutures are arranged to form a reinforcing portion 14 defined by the rows 12. The sutures may be nylon, silk, or other suitable material. Alternatively, the sutures may be replaced with the plastic, polypropylene, polyester, nylon or polymer material wires, bands, or filaments which are installed in the surface of the myocardium as shown in FIG. 8A.

Clinical assessment of the nature and extent of the heart dysfunction can indicate to what extent the heart muscle should be reinforced and also the appropriate location and configuration of the reinforcing portion 14. In FIG. 1, the reinforcing portion 14 is located in the myocardial surface of the left ventricle 15 of the heart 17. The reinforcing portion 14 may be used to correct a floppy aneurysm on the surface of the heart 17 caused by an infarct. Preferably, the method of the present invention may replace more extreme procedures such as ventricular remodeling or heart transplant to correct conditions such as cardiomyopathy or ventricular aneurysms. In any event, care must be taken to ensure that the sutures do not interfere with or occlude the coronary arteries 19 on the surface of the heart.

Figure 2:
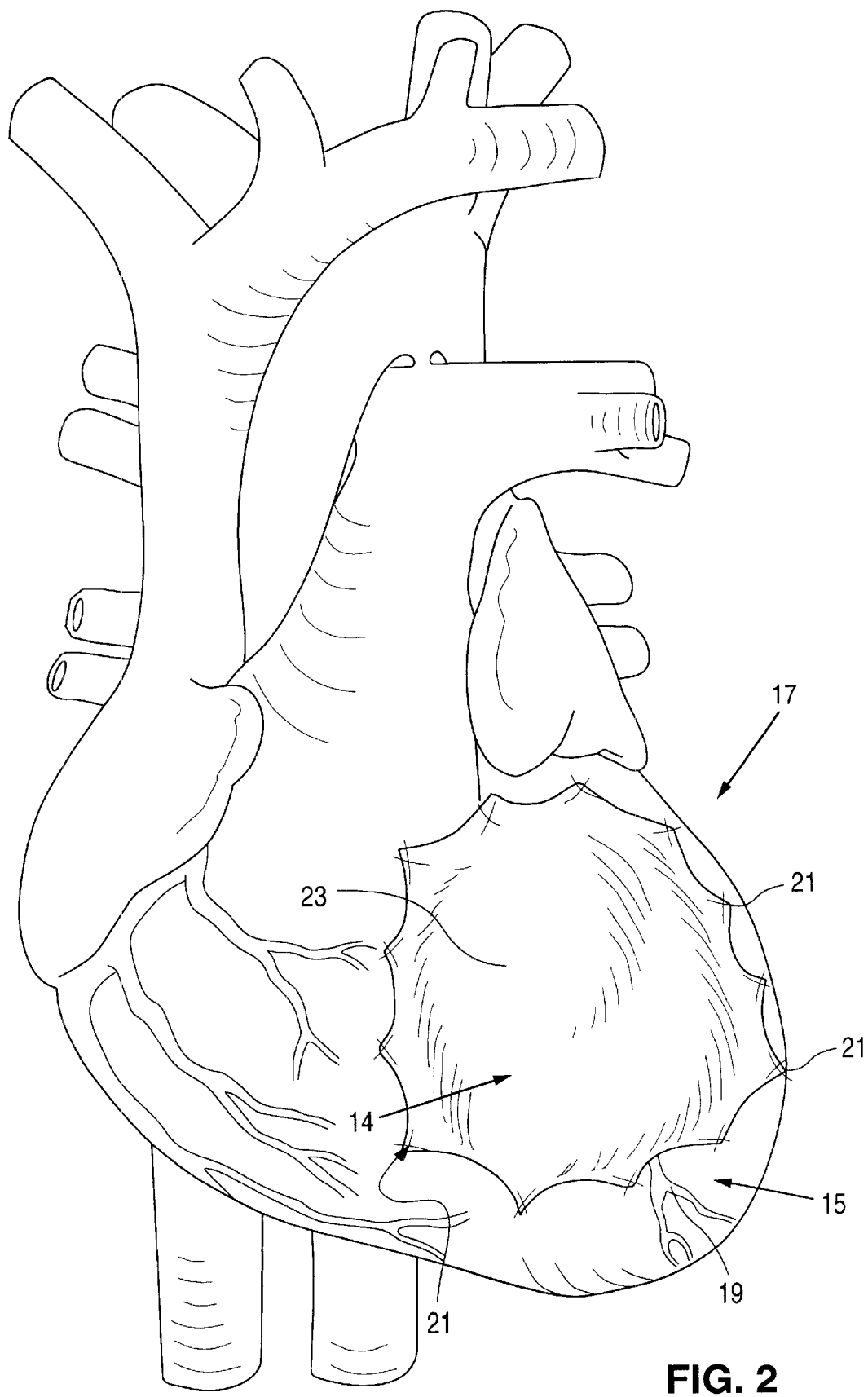
FIG. 2 is a passive ventricular assist device constructed in accordance with the teachings of the present invention comprising a section of material sewn onto a portion of a distended myocardium of a diseased heart in order to reinforce a weakened part of the ventricle.

FIG. 2 shows another embodiment of the present invention wherein a reinforcing portion 14 is created on the surface of the heart 17 using a flexible, rigid, or semi-rigid patch 23 of material fixed to the heart 17 using sutures 21 placed around the periphery of the patch 23 to form reinforcing portion. The patch 23 can be any one of a number of biocompatible materials, including: polyester fabric, pericardial tissue, and semi-rigid polymers. In a preferred method of the present invention, the heart 17 may be reinforced using a section of the pericardium (not shown) which is sutured or stapled to the surface of the heart 17 to form a reinforcing portion 14. Thus, the need for installation of a reinforcement device foreign to the patient's immune system is eliminated. In either embodiment, natural adhesions and scar tissue may be encouraged so that the myocardial tissue in contact with the patch 23 of reinforcement material or tissue is further stiffened to reduce wall motion of the heart tissue. The device of FIG. 2 is installed so as to improve the function of the left ventricle, however, it is apparent that the teachings of the present invention, including those embodiments previously and hereinafter described, may be configured so as to be applicable to the other chambers of the heart, including the right ventricle and the right and left atrium.

Figure 3:
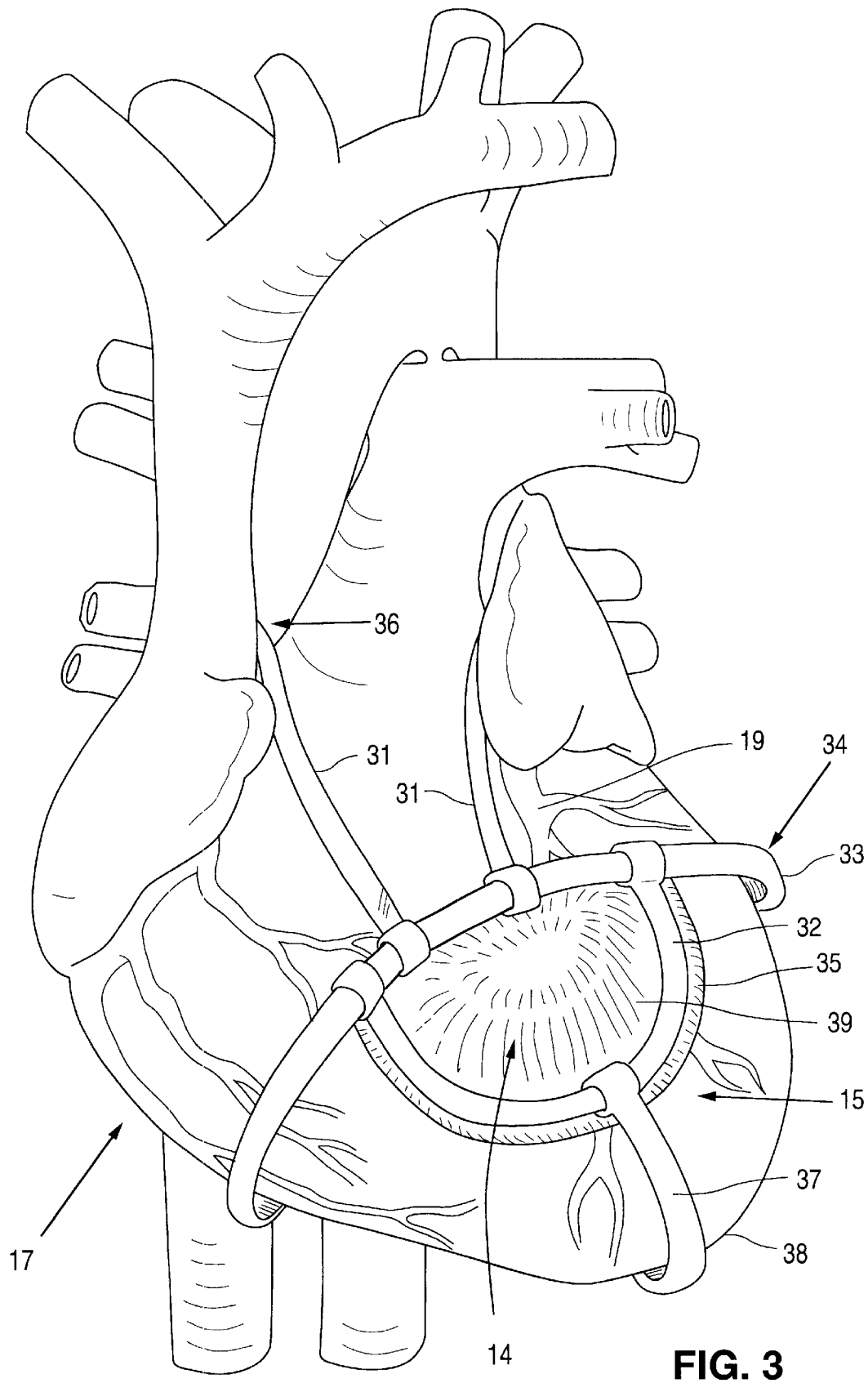
FIG. 3 is a passive ventricular assist device constructed in accordance with the teachings of the present invention wherein a basket shaped frame assembly having a pad assembly contacting a portion of a distended myocardium of a diseased heart is installed around the heart.

FIG. 3 is an alternative embodiment of the present invention wherein the reinforcing portion 14 is created using a pad assembly 39 installed in facing engagement with the surface of the heart tissue using a flexible, semi-rigid or rigid frame 34 wrapped around the heart 17. The flexible frame 34 may comprise a first support member 33 installed around the lower portion of the heart and encompassing the periphery of the heart as shown in FIG. 3. The embodiment of FIG. 2 also has a second support member 31 which is configured to pass through the transverse sinus 36 of the heart. The member 31 may either loop around the root of the aorta and then be reconnected to the lateral support member 33 as shown in FIG. 3, or it may be connected to a third support member 37 which passes over the apex 38 of the heart. The device of FIG. 3 further includes a horseshoe member 32 which is configured to retain the pad assembly 39 securely against the surface of the heart 17. A third support member 37 is fastened at a first end to the horseshoe member 32 and connects to the second support member 31 at the posterior side of the heart.

It is clear that the teachings of the present invention include a number of embodiments which perform substantially the same function as the frame shown in FIG. 3. The frame may be made of flexible straps of nylon, plastic, silicone, stainless steel, polyester fabric, pericardial tissue (either human, bovine, or porcine tissue), and other biocompatible biologic material. Other configurations are also possible, using different arrangements and orientations of the support members and straps of FIG. 3. For the embodiment of FIG. 3, it is only important that the pad assembly 39 be held securely against the heart tissue portion that is to be reinforced so as to control ventricular expansion in the reinforcing portion 14.

Figure 4B:
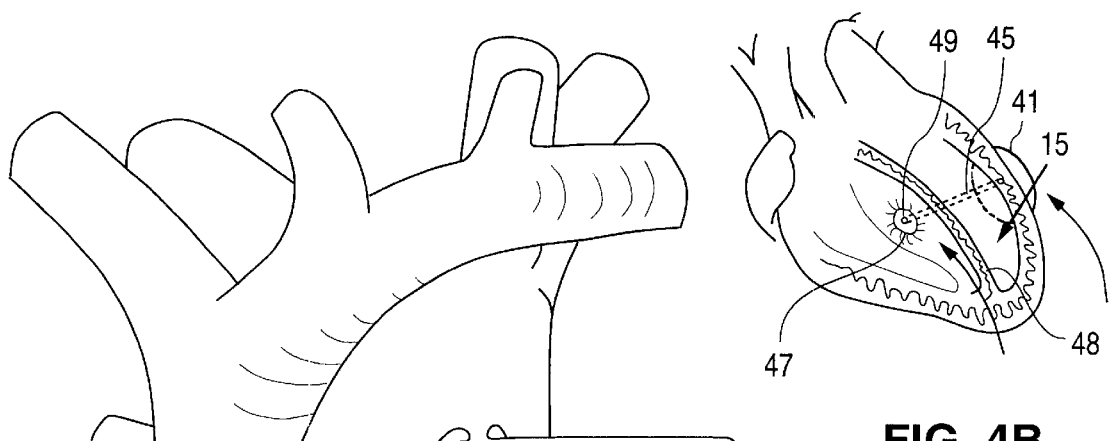
FIG. 4B is a sectional plan view of the device of FIG. 4A showing the anchor portion of the device in place in the septal wall of the heart.
Figure 4A:
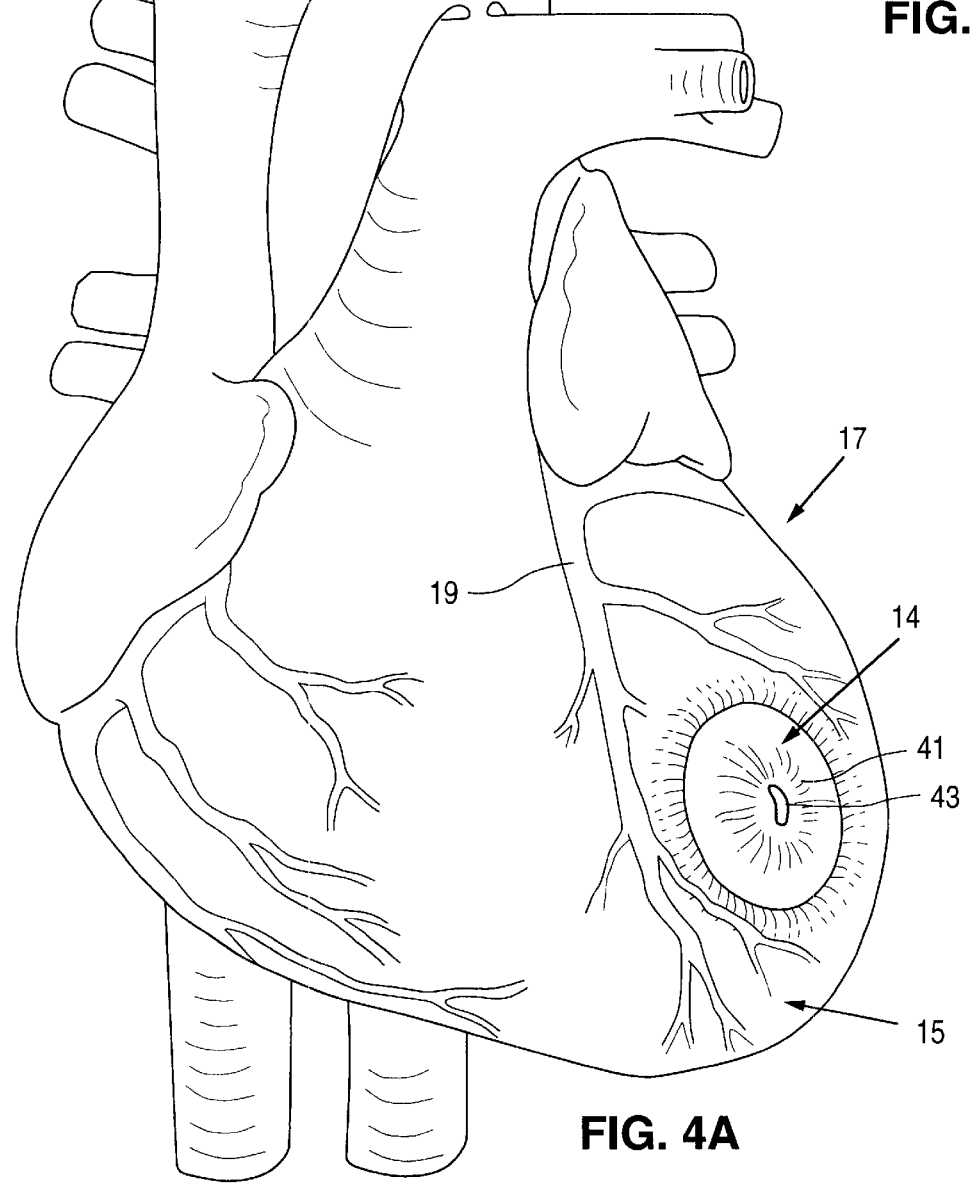
FIG. 4A is a passive ventricular assist device constructed in accordance with the teachings of the present invention showing a portion of a distended myocardium of a diseased heart being restrained using a pad assembly which is anchored to the septal wall of the heart.

FIGS. 4A and 4B show another embodiment of the present invention wherein the reinforcing portion 14 is created by installing a anchoring member 45 through the ventricular wall of the heart 17. The anchoring member 45 comprises a first portion having a reinforcement end 43 and a second portion having an anchoring end 49. For the configuration shown in FIG. 4, the anchoring end 49 is fastened to the interior septal wall 48 of the heart 17 opposite the reinforcing portion 14, however, the methods of the present invention comprise anchoring the anchoring member 14 to any body structure which is relatively fixed in relation to the portion of the heart to be restrained. The present invention also comprehends fixing the ventricular or atrial wall of the heart to the opposite atrial or ventricular wall so as to limit cardiac movement in the portion of the heart to be restrained.

The reinforcement end 43 is fixed to a pad assembly 41 which limits the ventricular expansion of the reinforcing portion 14 of the heart wall beyond the limits of the anchoring member 45. The anchoring member 45 may be a rod configured from stainless steel, nylon, silicone, or other biocompatible material. It may be substantially rigid or it may be flexible and it may also be configured from a material which allows some axial expansion, e.g. silicone. The member 45 may also be configured as a flexible tether, such as a stainless steel cable or a nylon or silk suture. Care must be taken to choose a material which resists thrombosis or to treat the anchoring member 45 in a manner which will prevent the formation of thrombotic material on the member 45 over time (e.g., heparin treatment).

Figure 4C:
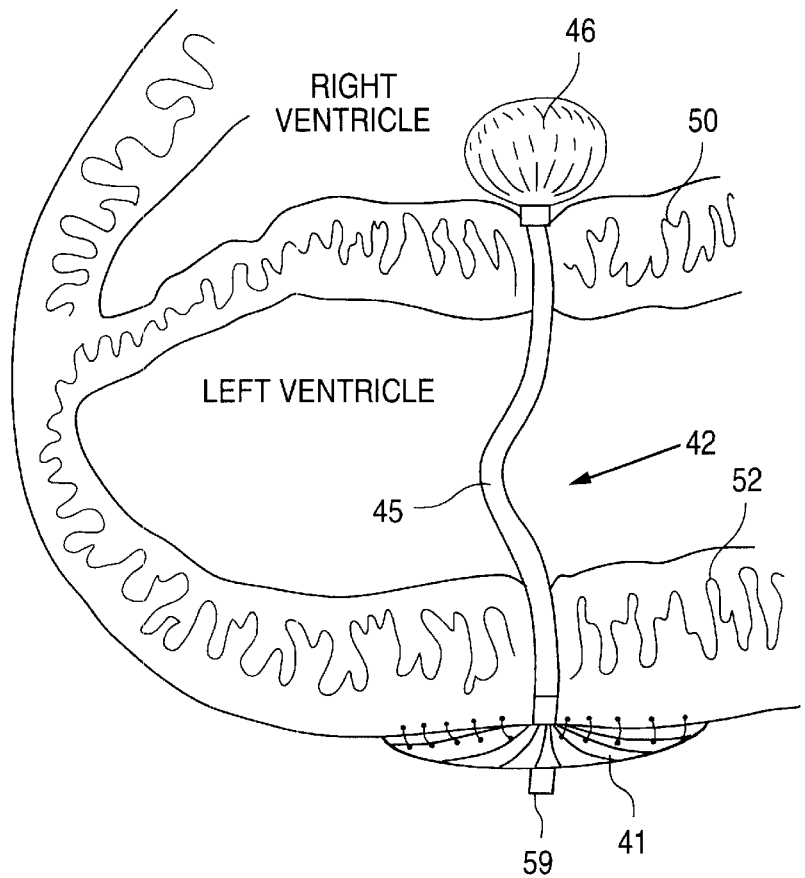
FIG. 4C shows an alternate embodiment of the device of FIG. 4A including an expandable member engaging the wall of the heart opposite the portion of the heart to be restrained.

FIG. 4C shows a preferred embodiment of a device for installation of a septally anchored cardiac assist device. The passive assist device 42 is shown installed to reduce the ventricular expansion of the left ventricle wall 52. The device 42 comprises an anchoring member 45 which may be configured to relatively flexible or substantially stiff depending on the clinical situation. Suitable materials include silicon, nylon, stainless steel, plastic, elastomeric materials, or a any such suitable biocompatible material. The anchoring member 45 is further provided with an inflation lumen therethrough in fluid communication with an expandable member 46 fixed to the distal end of the anchoring member 45.

The device 42 is preferably initially disposed with an insertion trocar sheath 58 prior to cardiac implantation. The sheath 58 comprises a tubular body 54 having a funnel shaped reinforcement end 66 which aids in the insertion of the assist device 42. The tubular body includes a sharpened anchoring end 56 which allows the trocar sheath 58 to be advanced through the myocardial surface and septal wall of the heart. The pad assembly 41 may have an umbrella configuration to limit the cross sectional area of the pad 41 to allow the assist device 42 to be inserted into the tubular body 54 of the trocar sheath 58.

Figure 4D:
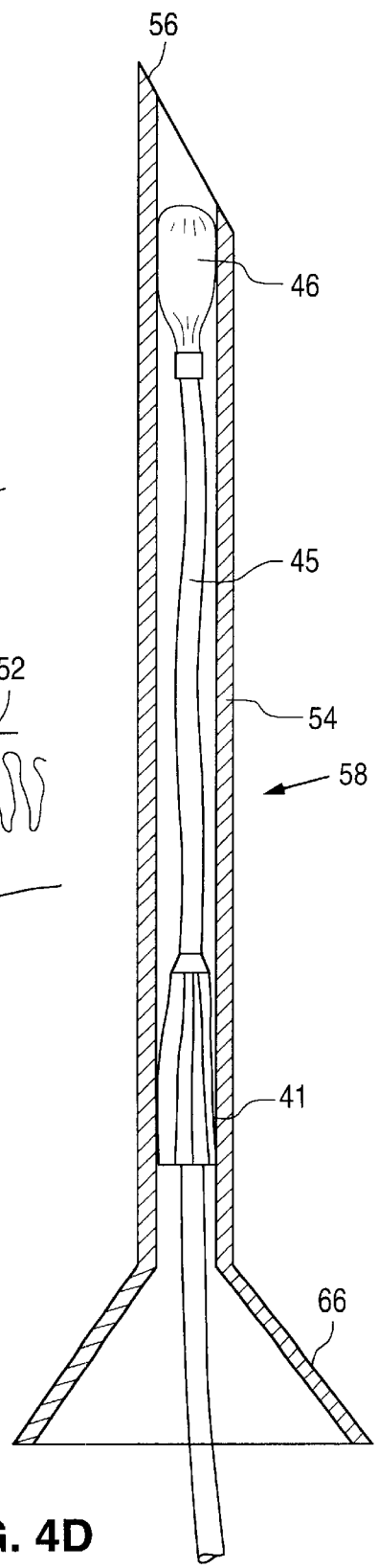
FIG. 4D is a plan sectional of the device of FIG. 4C installed within a trocar sheath.
Figure 4E:
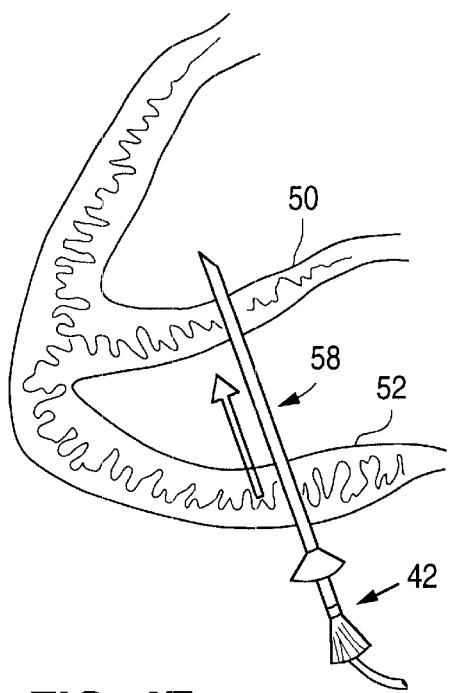
FIG. 4E is a graphical illustration of a method of the present invention for installing a device such as shown in FIG. 4D in the ventricle of a patient, showing the step of inserting the device into the ventricle.
Figure 4F:
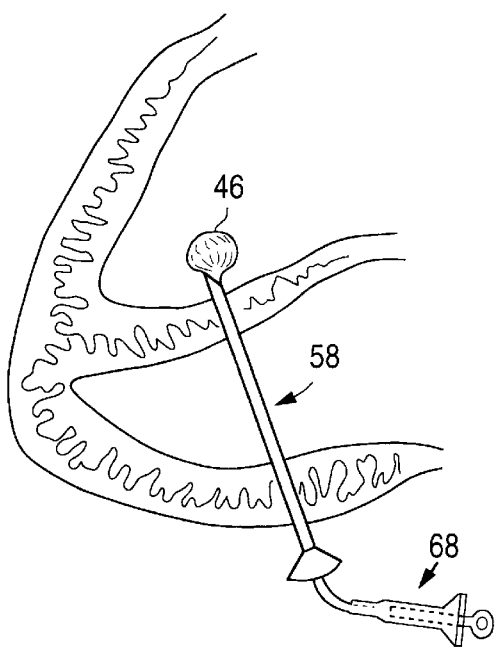
FIG. 4F is a graphical illustration of a method of the present invention for installing a device such as shown in FIG. 4D in the ventricle of a patient, showing the step of expanding the device.
Figure 4G:
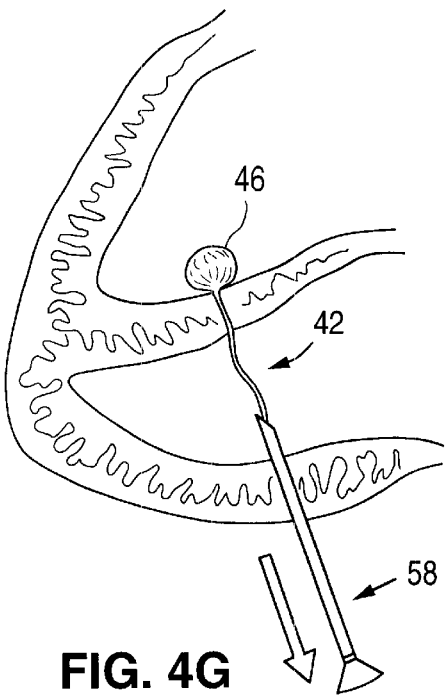
FIG. 4G is a graphical illustration of a method of the present invention for installing a device such as shown in FIG. 4D in the ventricle of a patient, showing the step of pulling the device proximally to contact the septal wall.
Figure 4H:
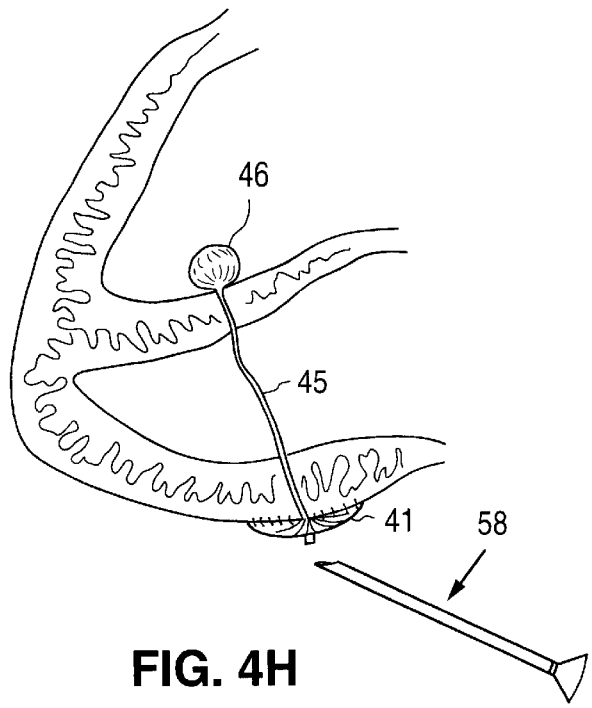
FIG. 4H is a graphical illustration of a method of of present invention for installing a device such as shown in FIG. 4D in the ventricle of a patient, showing the step of withdrawing a sheath from the device and anchoring the device.

FIG. 4E shows a method of use of the device of FIGS. 4C and 4D. In the first step, the trocar sheath 58, with the assist device 42 in place, is used to pierce the wall of the left ventricle 52 and is passed into the right ventricle through the septal wall 50. The assist device 42 may also be inserted into the trocar sheath 58 after the sheath 58 has been used to access the right ventricle of the heart. Alternatively, a stylet, scalpel, or other tool may be used to create a surgical access site penetrating the ventricular 52 and septal 50 wall. The assist device may then be advanced into the right ventricle through the surgical access site without the use of a trocar sheath. Installation without a trocar sheath may require that the material of the anchoring member 45 have sufficient column strength to be pushed into the heart muscle supported. The assist device 42 may be installed within the appropriate cardiac chamber using visual, tactile, fluoroscopic, or endoscopic guidance, for example.

Once the assist device 42 is situated correctly wherein the distal end of the device extends beyond the septal wall 50 of the heart, the expandable member 46 is expanded as shown in the second stage drawing of FIG. 4E. The expandable member 46 may comprise an inflatable balloon or an expandable foam which contracts when subjected to a vacuum. A syringe 68 is in fluid communication with the proximal end 59 of the assist device 42 and is used to provide saline or other suitable inflation fluid and may be used to provide a vacuum for an expandable foam configuration.

In the third step of the process, the assist device 42 is pulled proximally so that the expandable member 46 contacts the septal wall. If the assist device 42 was installed with the aid of a sheath 58, the sheath 58 may be withdrawn and the pad assembly 41 is deployed from within the trocar sheath as shown in step 4 of FIG. 4E. The pad assembly 41 is sutured, stapled, glued, or otherwise fixed to the myocardial surface and the anchoring member 45 is fixed in relation of the pad assembly 41. Preferably, the surgeon will assess the degree of cardiac assistance required and the adjust the length of the anchoring member 45 accordingly to provide the appropriate degree of cardiac restraint.

Figure 5:
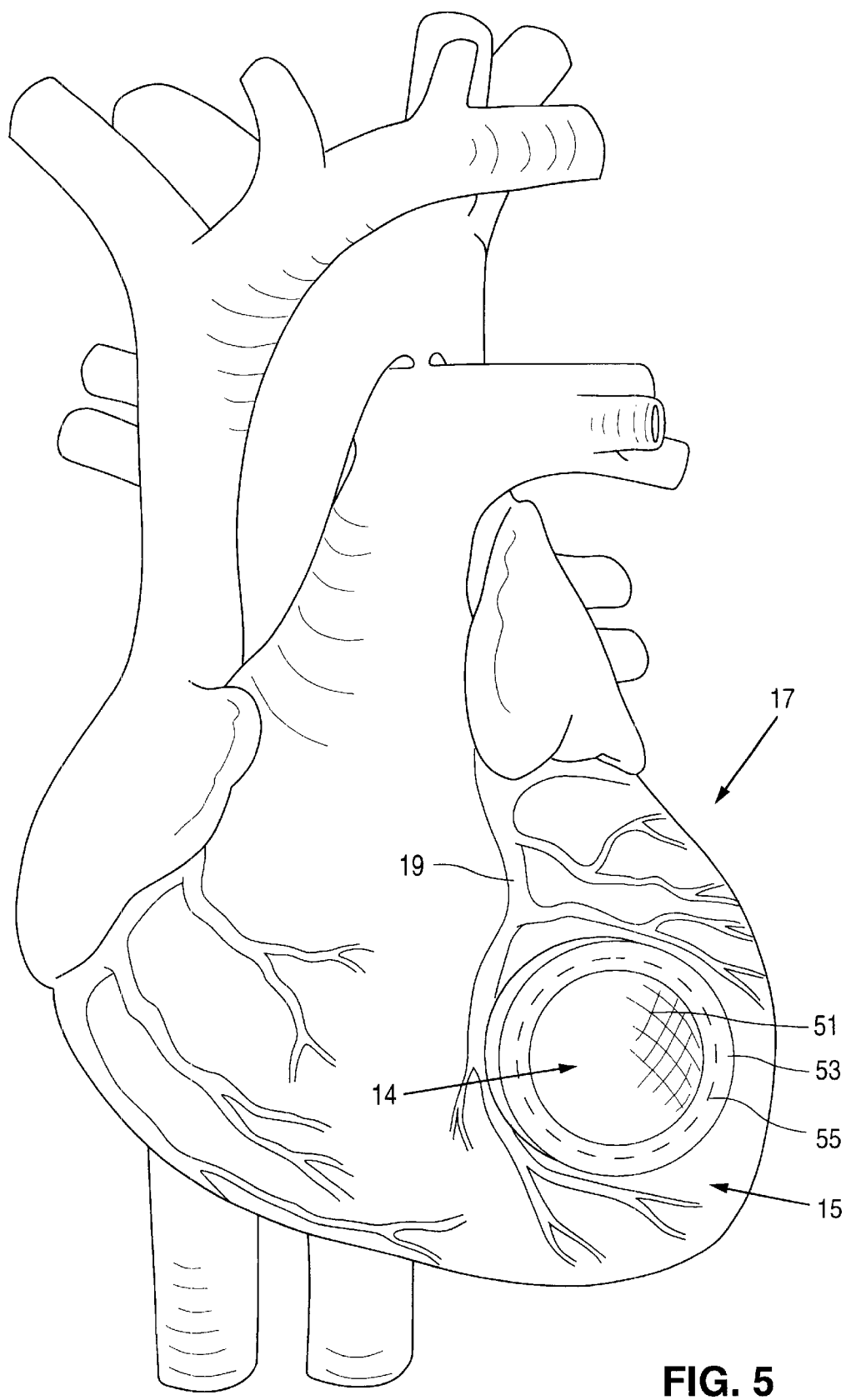
FIG. 5 is a passive ventricular assist device constructed in accordance with the teachings of the present invention showing an annular ring assembly sewn to a portion of a distended myocardium of a diseased heart to reinforce the heart and restrain the diseased portion of the myocardium.

FIG. 5 is another alternative embodiment of the present invention. The device of FIG. 5 comprises a relatively stiff annular ring 53 which is fastened to the myocardium of the heart 17 using a series of sutures 55 around the periphery of the ring 53. The ring 53 may also be fastened using staples, tissue adhesive, rivets, or other suitable fastening means well known in the art. The reinforcing portion 14 may also be covered by an interior portion 51 of the annular ring. The interior portion 51 can be configured from a variety of materials, including: metals, polymers, fabric mesh, perforated materials, or elastomeric material. The interior portion 51 and the annular ring 55 cooperate to reinforce the heart tissue and limit ventricular expansion of the reinforcing portion 14. For ventricular control of the left heart, the device is preferably configured to avoid interfering with or occluding the coronary arteries 19. The configuration of the passive ventricular assist device may also be such that the natural formation of adhesions and scar tissue in the reinforcing portion 14 is encouraged so as to further stiffen and reinforce the tissue of the reinforcing portion 14. This can be accomplished for example, by providing a mesh or screen that will naturally be encased in scar tissue, or causing irritation with a roughened surface, little dimples, etc., or coating the device (or separately applying) an irritating or adhesion-promoting chemical.

Figure 6:
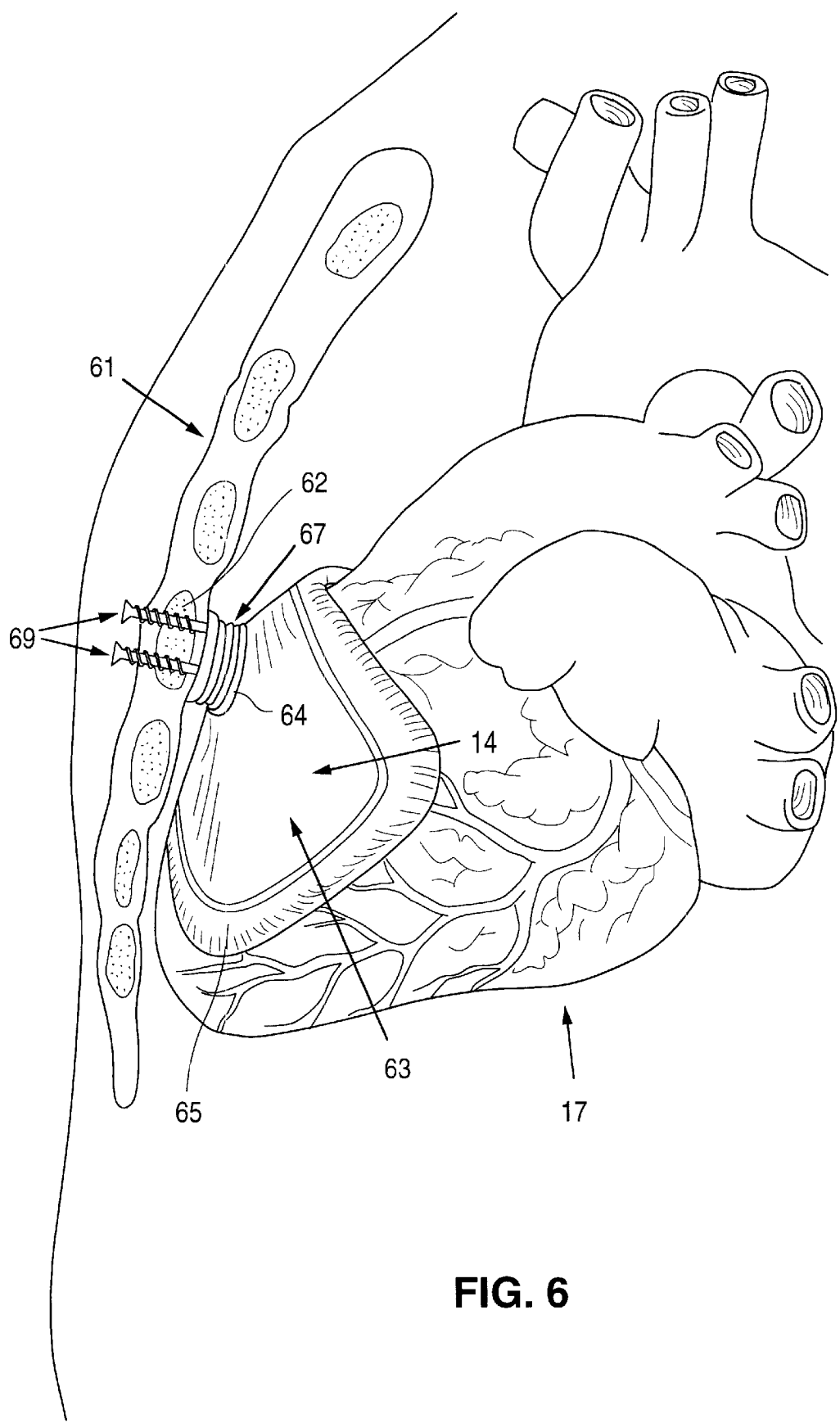
FIG. 6 is a passive ventricular assist device constructed in accordance with the teachings of the present invention having a base portion contacting a distended portion of a myocardium of a diseased heart wherein the base portion is anchored to the sternum or ribs of a patient.

FIG. 6 shows a preferred embodiment of the present invention configured to limit ventricular expansion of the left heart. A reinforcing portion 14 is created using a pad assembly 65 held in place against the heart tissue to be reinforced with a relatively rigid base member 63. The base member 63 is fixed to a body structure which is relatively fixed in relation to the ventricular or atrial expansion of the heart 17. In the configuration shown in FIG. 6, the base member 63 is fixed to an adjustment mechanism 67 which in turn is fixed to a rib 62 of the patient with a pair of screws 69. The device may also be fixed to the sternum 61 of the patient. It is only important that the body structure chosen be relatively stable in relation to the movement of the heart 17.

The adjustable mechanism 67 is configured to allow an increase or decrease in the pressure exerted on the reinforcing portion 14 by the base member 63 and the pad assembly 65. The mechanism 67 of FIG. 6 includes a coil spring 64 which helps to prevent sudden pressure on the heart 17 during patient movement. The passive ventricular assist device can also be configured so that the pad assembly 65 is inflatable, thus allowing the surgeon to clinically determine the appropriate amount of pressure to exert on the reinforcing portion and then inflate the pad assembly appropriately. An inflatable pad assembly 65 also improves the fit of the device, especially considering the variety of heart sizes and shapes that are exist in the patient population. For this reason, the base member 63 may be configured from a relatively ductile material which will allow the surgeon to bend and shape the member 63 to form a more secure fit between the heart 17 and the portion of the heart muscle to be reinforced. The inflatable pad assembly 65 may also be configured to allow subsequent inflation or deflation of the pad assembly 65 as the clinical situation indicates, either with or without further surgical intervention. Alternatively, the inflatable pad assembly 65 could push directly on a non-moving body structure, eliminating the need for base member 63.

Figure 7:
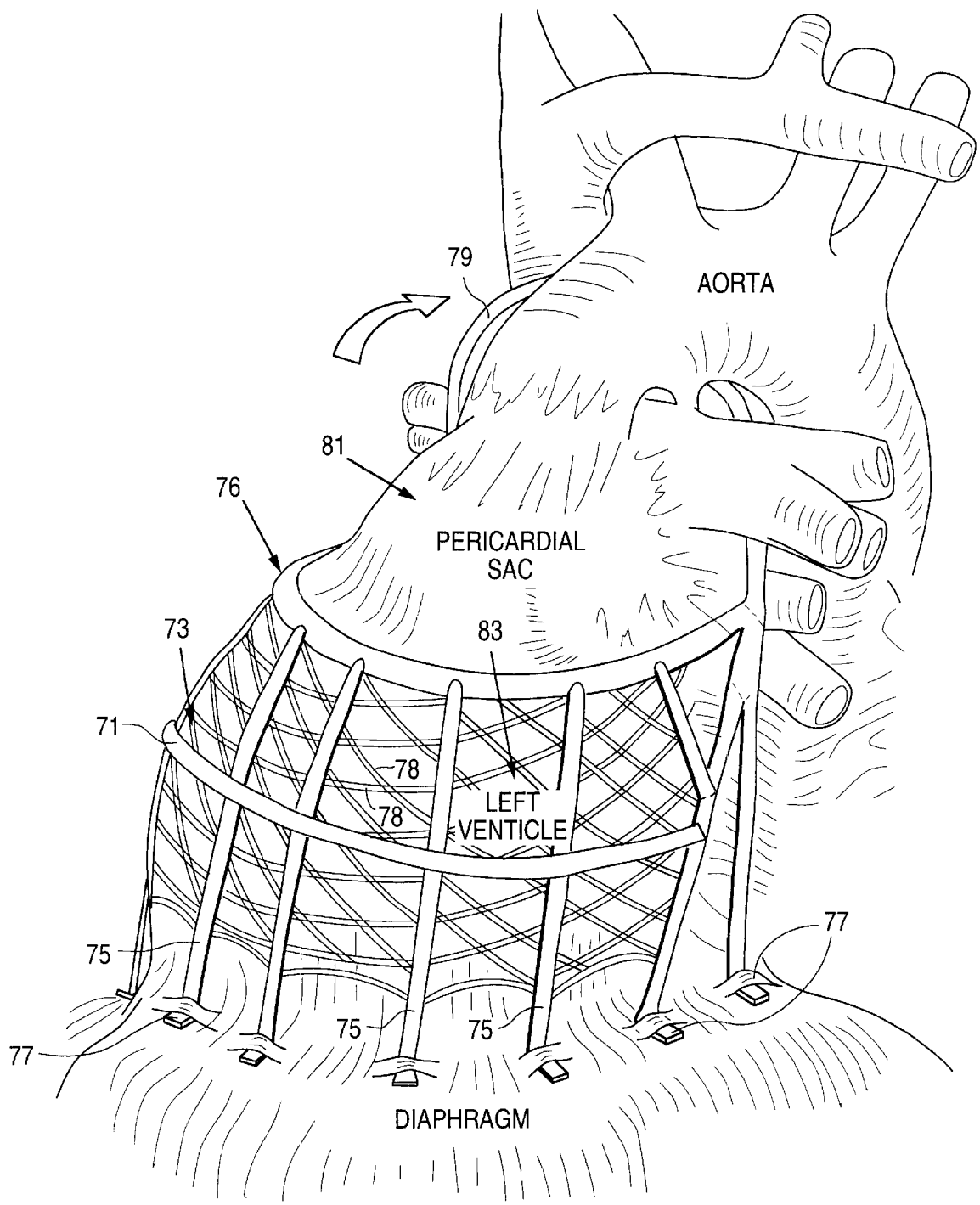
FIG. 7 is a passive ventricular assist device constructed in accordance with the teachings of the present invention comprising a harness assembly installed around the pericardial sack of a diseased heart, the harness comprising a number of flexible straps between which is disposed a mesh limiter configured to restrain a portion of the diseased heart.

FIG. 7 is another embodiment of the present invention wherein the heart muscle is reinforced using a frame 76 coupled with a net 73 to limit ventricular expansion of the heart. The frame 76 comprises one or more lateral 71 and vertical 75 support members. The support members may be any number of materials including polymer, metal, fabric, and elastic and may be made either substantially rigid, flexible, or bendable as the clinical situation indicates. The net 73 and the frame 76 may be made from relatively flexible material such as polyethylene, DACRON™, nylon, silk, PVC, or other biocompatible materials. Alternatively, the net 73 or frame 76 may also be made relatively rigid but bendable to allow the passive ventricular assist device to be custom bent inward by the surgeon to place pressure on specific areas of the heart muscle so as to create a reinforcing portion (not shown) at which ventricular expansion is limited. The device shown in FIG. 7 is held in place with a retaining strap 79 which is threaded through the transverse sinus and is fastened at both ends to a lateral member 71 of the frame 76. Care must be taken when threading the retaining strap 79 to avoid damaging the phrenic nerve and other structures within the transverse sinus 38. The device of FIG. 7 is shown in place around a heart with the pericardial sack left intact to prevent damage to the tissue surface from contact with the device.

Figure 9:
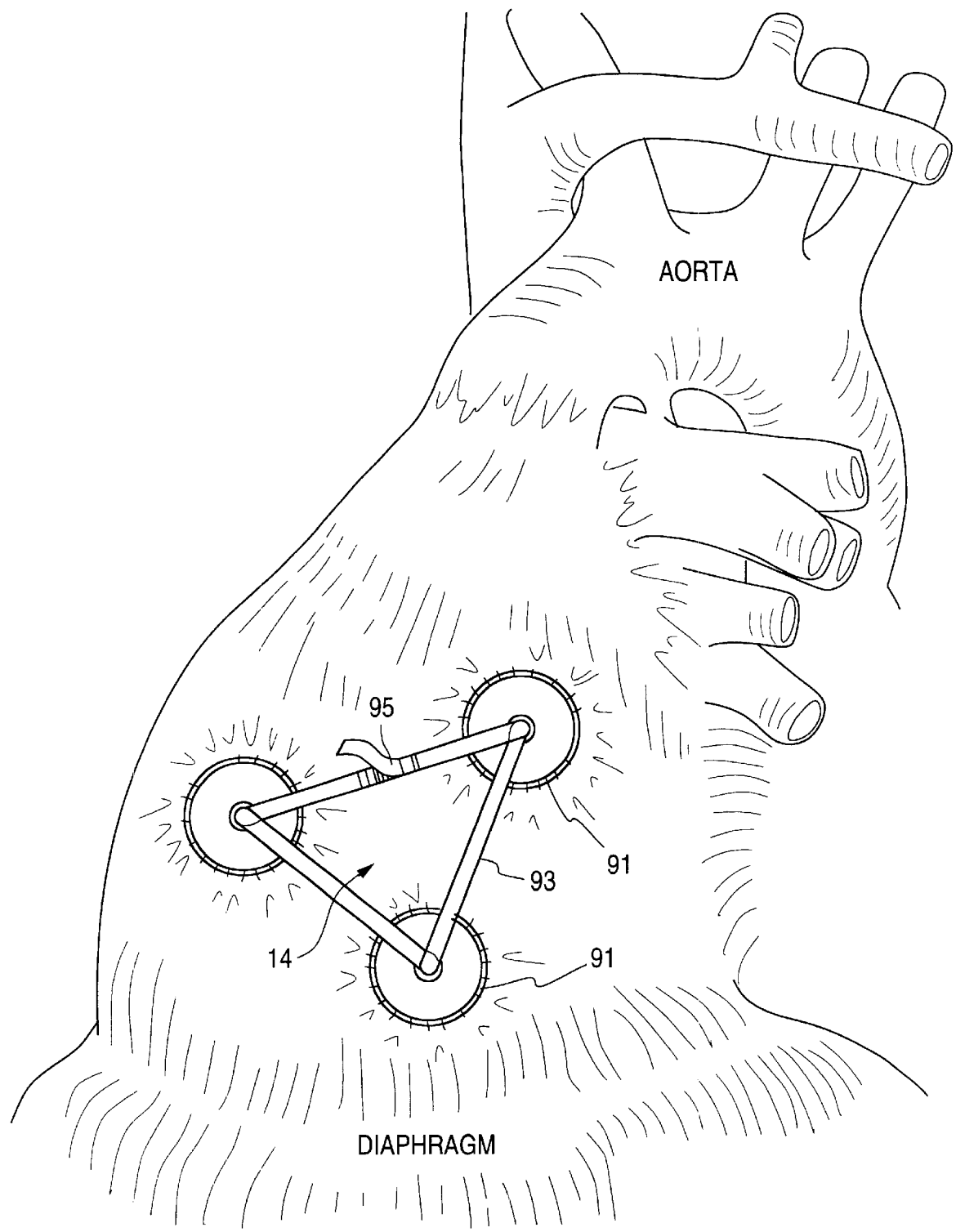
FIG. 9 shows a passive ventricular assist device constructed in accordance with the teachings of the present invention wherein the device comprises three external pads installed on the surface of the myocardium and joined by strap members.

FIG. 9 shows another embodiment of the present invention wherein a reinforcing portion 14 is formed by installing a number of pads 91 onto the surface of the myocardium. The pads 91 are interconnected using straps 93 which can be tightened using a tightener 95 to reduce the distance between the pads 91. The tightener can be a traditional buckle, a ratcheting mechanism, a pull tab, or any well known means to ensure adequate tension in the straps 93. Myocardial expansion is reduced in the reinforcing portion 14 by putting sufficient tension on the straps 93 such that the pads 91 are not allowed to expand and separate during ventricular or atrial expansion. The pads may be secured to the myocardial or pericardial surface using sutures, staples, rivets, tissue adhesive, or other well known surgical fastening means. The straps may be made from nylon, elastic or inelastic polymers, silk, silicone, plastic, or other biocompatible material well known in the art. The device may comprise only two pads 91 or it may be configured with 3 or more pads as the clinical situation indicates without departing from the teachings of the present invention.

Preferably, the devices of the present invention will be used to augment cardiac flow from a diseased heart. Often, it will be desirable to install the device concurrently with performing other cardiac repairs as this eliminates multiple surgical procedures on the patient and may further enhance cardiac performance. For example, installation of the device can be accomplished concurrently with a valve repair procedure to repair or replace leaky or malfunctioning valves in the heart. Installation of a passive ventricular assist device constructed according to the teachings of the present invention can also be accomplished concurrently with a coronary artery bypass graft (CABG) procedure. The device may also be installed using an intraoperative catheter procedure as described in copending patent application Ser. No. 08/752,741.

The present invention also encompasses methods for passive cardiac assist to improve cardiac output by reinforcing a portion of the cardiac muscle. The first step in a method of the present invention is to provide access to the heart. As discussed above, this can be done using traditional surgical procedures, e.g., a sternotomy or thoracotomy; minimally invasive surgical techniques, e.g., mini-sternotomy, mini-thoracotomy; or endoscopically through a small trocar port or incision, or a major vein or artery of the patient. Access may also be provided using a sub-xyphoid or xyphoid approach as described in U.S. patent application Ser. No. 09/071,757, incorporated herein by reference in its entirety.

The type of access provided will also be affected by whether the procedure is to be accomplished on a stilled heart supported by cardiopulmonary bypass, on a beating heart, or on a beating heart partially supported by a cardiac assist device. Although it is known in the art to perform CPB endoscopically, most often the procedure is performed with an open chest using a full sternotomy. Beating heart procedures can be performed with an open chest or using minimally invasive surgical (MIS) techniques. Beating heart using MIS is preferable because of the decreased trauma and recovery time that is required by the procedure as well as the fact that with the heart beating, it will be easier to assess the effects of a given PVAD configuration. Additional room in the chest cavity may be provided by partially unloading one or both sides of the heart with a cardiac assist device, because upon unloading the heart, the heart becomes deflated similar to a heart on full CPB.

Once suitable access has been provided, the next step is to clinically the determine the location and extent of reinforcement required. Such a determination will preferably consider whether reinforcement will be required on one or both sides of the heart, whether reinforcement of the atrial or ventricular walls will be required, and what method or device of reinforcement will be best suited for the clinical application.

Following a clinical determination of the nature, extent, and location of the reinforcement required, the next step is to reinforce a portion of the heart tissue so as to limit atrial or ventricular wall motion and increase cardiac output. This can be accomplished using any one of the previously described methods or devices. Again, clinical indications will generally determine the proper means of heart reinforcement.

Installation of the one of the previously described embodiments may be used to reinforce the heart tissue to limit atrial or ventricular expansion. For example, the wall of the heart to be reinforced may be fixed to a body structure which is relatively stable compared to the reinforcing portion of the heart. The structure chosen can be the ribs, sternum, diaphragm, or it may be a wall of the heart opposite the muscle tissue to be reinforced in the reinforcing portion (e.g., the septal wall). Additionally, the heart may be reinforced using a material which is injected into the tissue of the heart muscle that is to be reinforced. For example, a polymer which hardens following injection into the muscle can be used to limit ventricular or atrial expansion. Also, a material which encourages the formation of scar tissue may be used to harden a portion of the heart muscle that is to be reinforced. Thrombin or collagen material are two possible materials for such an application wherein the material is injected into the reinforcing portion. Another reinforcement could consist of metal or plastic threads, wires, or filaments embedded in the myocardium.

Figure 10:
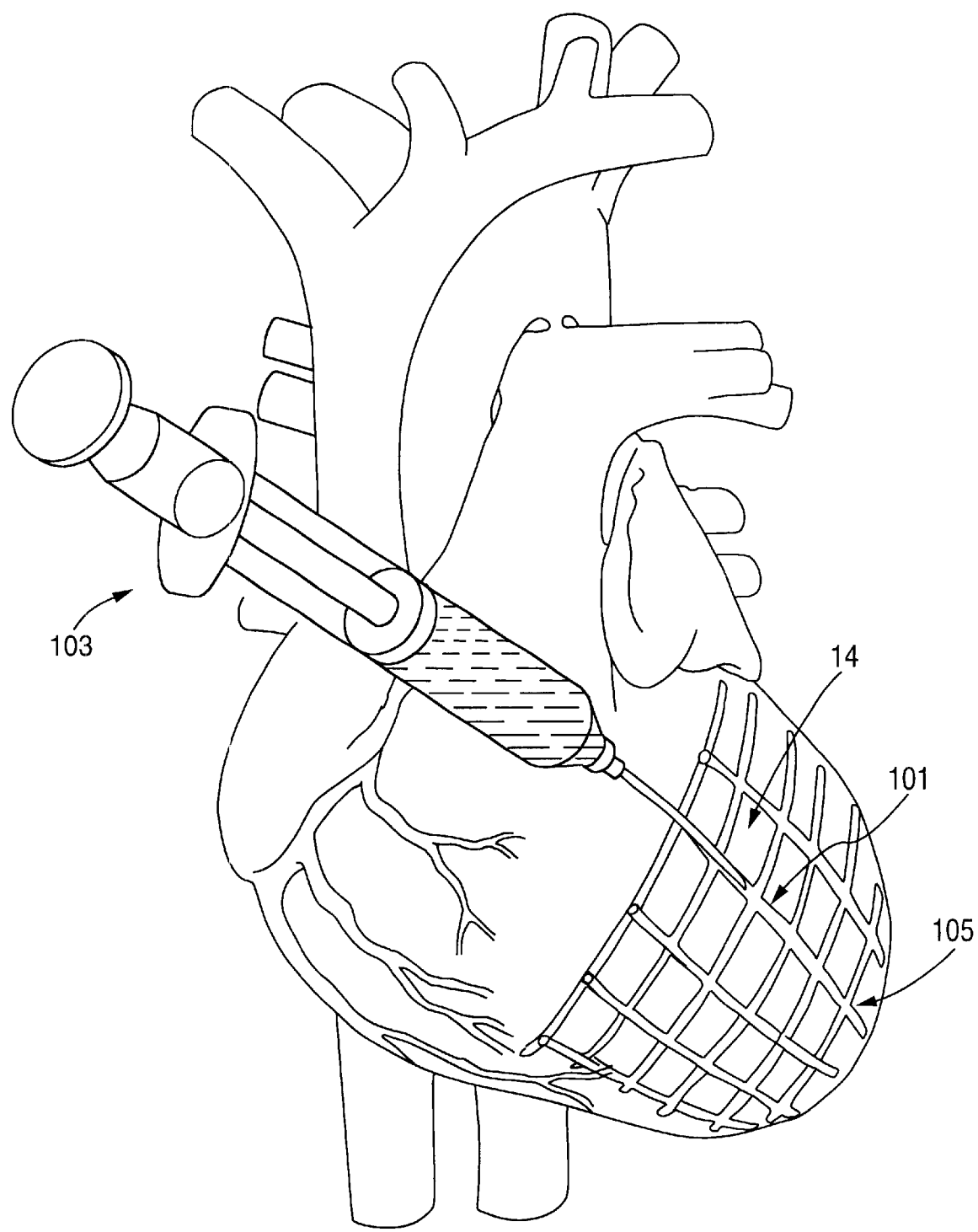
FIG. 10 shows a method of passively assisting cardiac function by forming a grid pattern on the myocardial surface by injecting a procoagulant material onto the surface of the heart.

As shown in FIG. 10, a grid pattern may be configured to create a reinforcing portion 14 on the surface of the heart. These could also be injected, rather than laid in the surface on other embodiments. A syringe is used to inject an thrombotic or procoagulant material into the myocardium of the heart to form a grid 105 of hardened furrows 101. These furrows 101 may be formed by incising grooves in the surface of the heart with a cutting instrument or ablation element which are subsequently filled with the procoagulant material. The material may also be injected into a series of hypodermic needle holes and allowed to harden.

The grid 105 may also be formed by making tunnels in the surface of the myocardium using lasers, needles, ablative tools or other well known elements. These tunnels may then be filled with the procoagulant material which is allowed to harden. For example, a tunnel may be formed in the myocardium by inserting a long syringe needle into the myocardium and then advancing the needle under the myocardial surface keeping the needle parallel to the surface so that the needle tip does is not allowed to exit. The needle can then be withdrawn from the newly formed tunnel simultaneously with filling the tunnel with procoagulant from the syringe as the needle is withdrawn. The formation of scar tissue in the reinforcing portion serves to thicken the muscle tissue and limit expansion of the tissue to increase cardiac output.

The clinical situation may indicate reinforcement of the heart tissue in more than one location is required. A reinforcing portion may be required in one or both ventricles, a ventricle and an atrium, one or both atria, or any combination thereof. The size of the reinforcing portion will also vary depending on the clinical situation. Repair of a floppy aneurysm may only require that the affected tissue be reinforced. Correction of severe cardiomyopathy may require a more substantial reinforcement in order to appropriately reinforce the tissue.

Following reinforcement of the heart tissue using the devices and methods of the present invention, the surgeon will generally test the patency and effectiveness of the procedure. This can usually be done by measuring the cardiac flow from the heart out the outflow tract. For a stilled heart procedure, this will require that the surgeon restart the heart by terminating cardioplegia flow to the heart and removing the patient from the CPB machine. It is usually desirable that the heart be beating during the duration of the procedure so that the surgeon can have a continuous indication as the clinical effects of the passive cardiac assist procedure. Once the surgeon has determined that the procedure is effective, the surgical access site may be closed and the patient allowed to recover normally.

For some patients, the clinical situation may indicate the need for additional procedures on the heart before restarting the heart (if on CPB) and closing the surgical access site. Valvular repair and CABG are two examples of possible procedures which could be performed in conjunction with the teachings of the present invention. Reinforcement of a portion of the heart may change the architecture of the heart and may increase leakage from already faulty heart valves, further increasing the need to perform additional repairs. The clinical situation may also be improved by the performance of the procedure. Ventricular enlargement can be corrected with the procedure and mitral valve function may be improved so that a mitral repair procedure is not necessary.

Figure 11A:
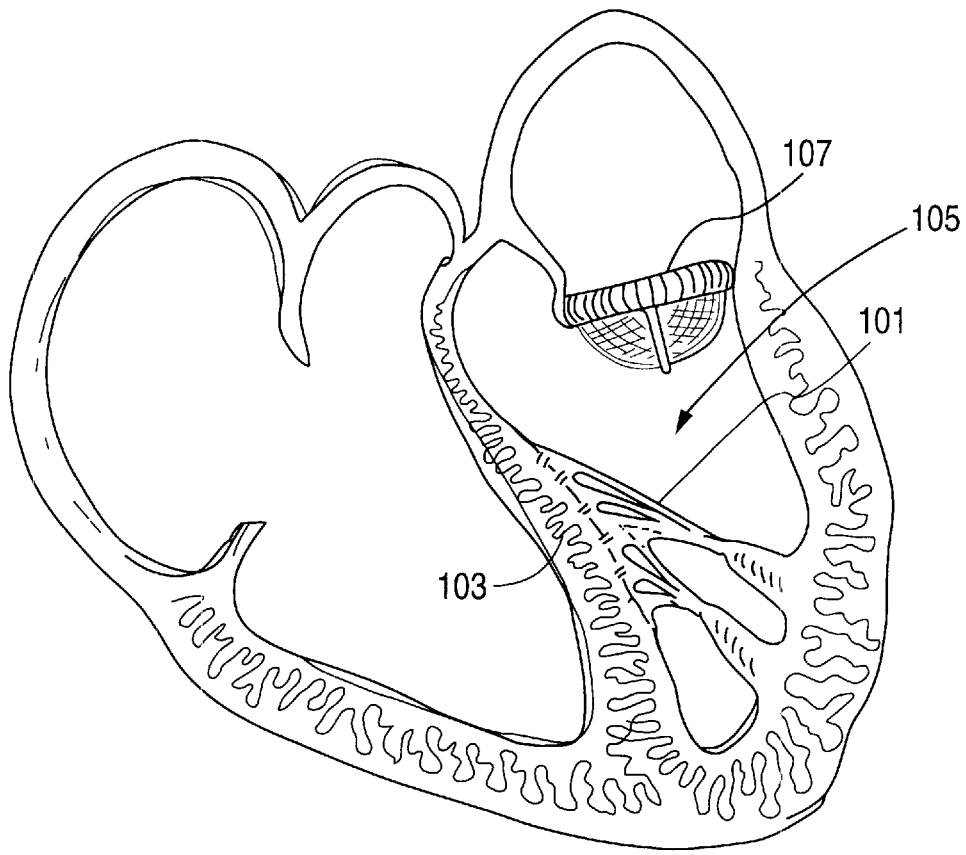
FIG. 11A shows a method of the present invention for passively assisting the left ventricle of the heart practiced in conjunction with a mitral valvular replacement procedure wherein a portion of the heart to be restrained in fixed to the septal wall of the heart using the tendineae chordae of the ventricle.
Figure 11B:
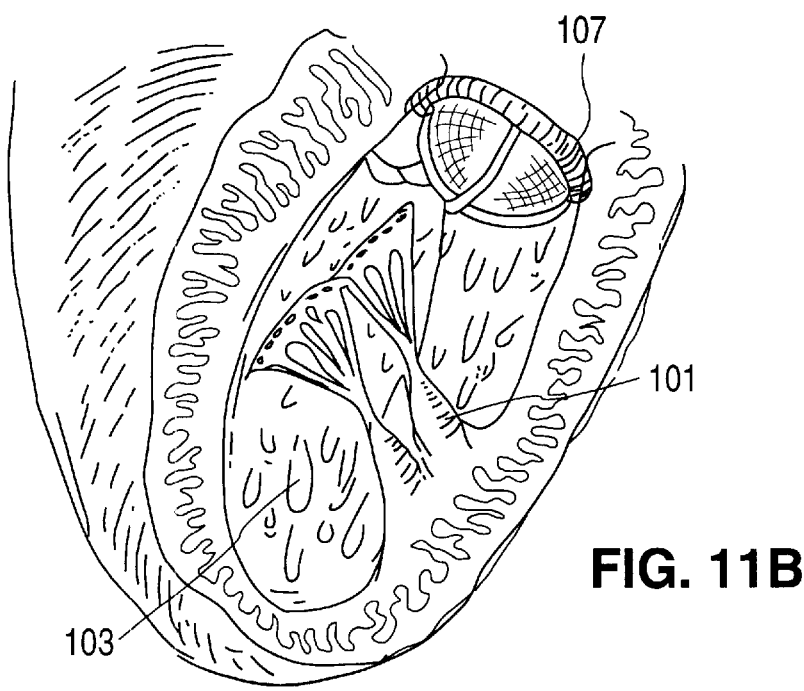
FIG. 11B is another view of the method of FIG. 11A.

FIGS. 11(A–B) show a method of the present invention wherein a mitral valve replacement procedure is accomplished concurrently with providing passive ventricular assistance to the left heart. The heart will normally be stopped and the patient will be supported using a cardiopulmonary bypass machine for a valvular replacement procedure. Access may be provided to the mitral valve as discussed above (i.e. sternotomy, thoracotomy, sub-xyphoid, minimally invasive access) or using endoscopic techniques. For example, access is possible through using a catheter inserted into the femoral vein to the inferior vena cava to the right atrium or from the carotid vein to superior vena cava to the right atrium. From the right atrium, the left atrium and mitral valve may be accessed transeptally. Access is also possible directly to the left ventricle from the aortic arch.

After surgical access has been provided as discussed above, a portion of the ventricle of the heart is restrained as shown in FIG. 11A, wherein the chordae tendineae 101 are severed from the diseased mitral valve and are subsequently sutured to the septal wall 103 of the heart. Clinical indications are assessed by the surgeon to determine the appropriate length of the chordae tendineae 101. The length of the tendineae 101 effectively controls the degree of ventricular restriction and the resultant effect on cardiac output. The tendineae 101 may also be sutured, stapled, glued, or otherwise fixed to the septal wall 103 without departing from the spirit of the invention. Alternatively, a series of sutures or other biologically acceptable attachment members, including donor tissue, nylon or elastomeric bands, and other biocompatible materials, may be used to fix the internal wall of the ventricle 105 in relation to the septal wall 103 to limit ventricular expansion of the heart wall.

Once the ventricle is appropriately reinforced, the diseased mitral valve is replaced with a prosthetic replacement valve 107. Replacement of the tricuspid valve concurrently with reinforcing a portion of the right ventricle with the chordae tendineae is similarly accomplished by using well known right heart access techniques. Valvular replacement procedures are well known in the art and more fully described in U.S. patent application Ser. No. 08/801,129, incorporated by reference herein in its entirety. Preferably, the valve procedure will be accomplished following the ventricular assist procedure so that the altered geometry of the ventricle will not affect the fit of the replacement valve 107.

As mentioned above, a serious complication of cardiomyopathy and other heart diseases is an enlarged (hypertrophic) heart. An enlarged heart is very inefficient at properly pumping blood. A large amount of ventricular "dead space" exists wherein the blood volume of the ventricle is not fully expelled with each contraction of the ventricle. The unexpelled blood reduces the amount of oxygenated blood that is provided to the patient's vascular system and can result in severe complications to the health of the patient. The teachings of the present invention include devices and methods for reducing the ventricular volume of the heart.

Figure 12A:
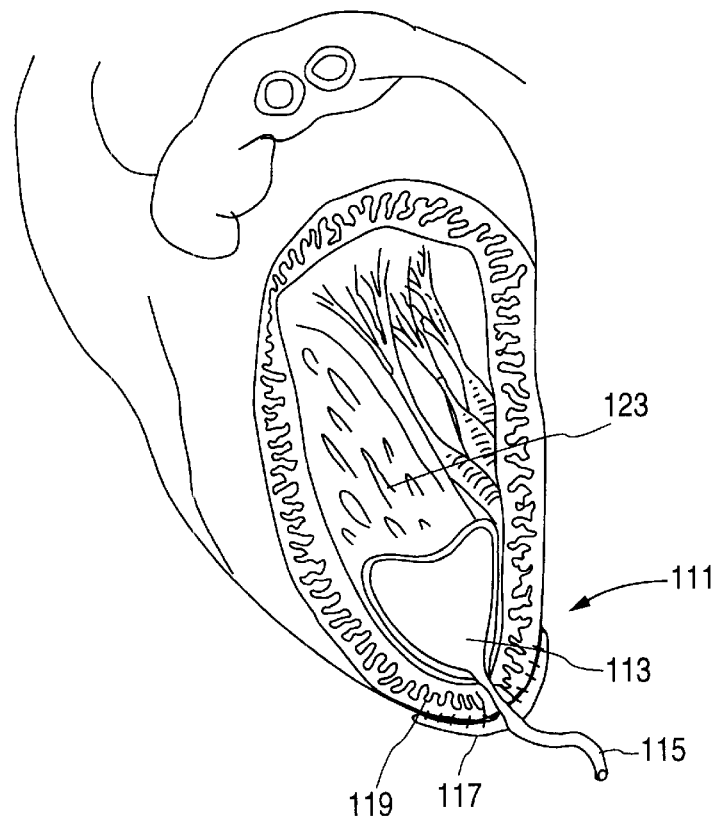
FIG. 12A is a cutaway view of the left ventricle of a patient showing an intra-ventricular volume displacement device installed within the apex of the ventricle.
Figure 12B:
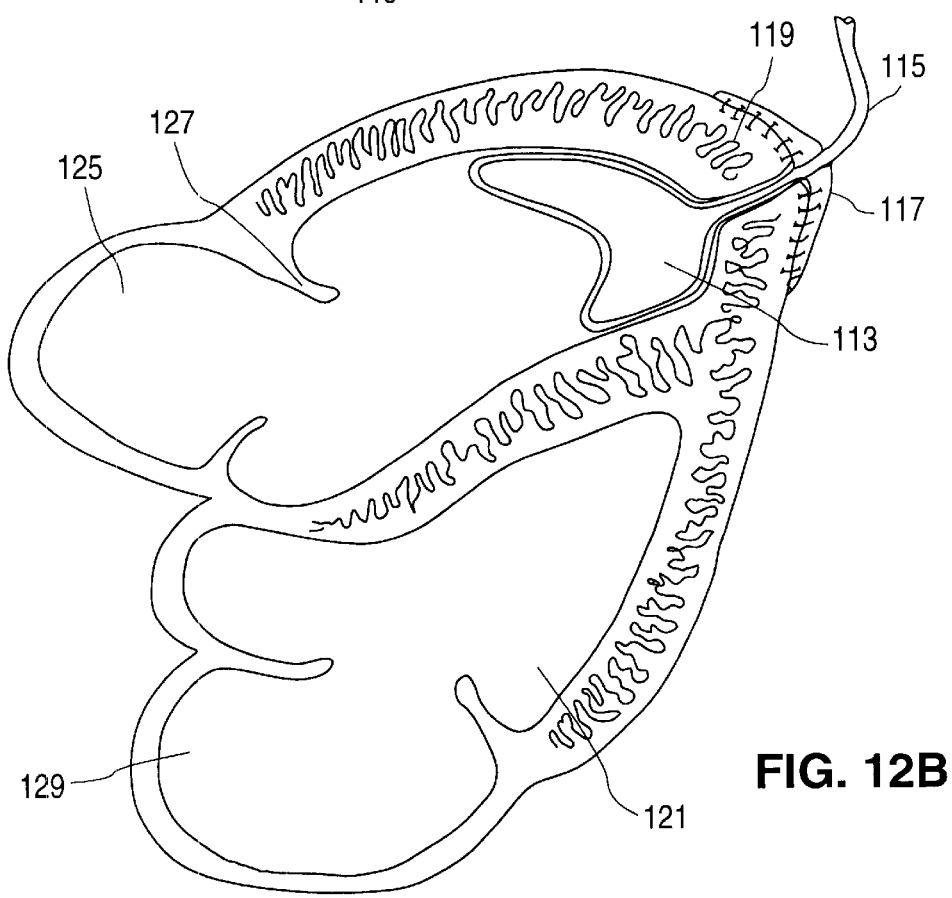
FIG. 12B is a cutaway view of the heart of the patient showing an intra-ventricular volume displacement device installed within the apex of the ventricle.

FIGS. 12(A–B) show a device of the present invention configured to reduce the ventricular "dead space" within an enlarged or weakened heart. An intra-ventricular volume displacement device 111 comprises an expandable member 113 which is installed in the apex 119 of the left ventricle 123 and expanded to reduce the blood volume of the ventricle 123. The expandable member 113 may be pre-shaped as shown in FIG. 12A to more closely approximate the appropriate ventricular geometry of a healthy heart. The expandable member 113 may be an inflatable balloon which is installed in the heart in an uninflated condition and then inflated with saline fluid, water, or other well known inflation fluids. The expandable member 113 may also comprise a low-density expandable foam which is maintained in an unexpanded condition by subjecting the member to a vacuum. Release of the vacuum causes the expansion of the member and a consequent reduction in the effective blood volume of the diseased heart. Suitable materials for the expandable member include silicone, various elastomers, and polytetrafluoroethylene (PTFE).

In one method of installation of an intra-ventricular volume displacement device 111 configured to reduce the left ventricular volume of the diseased heart, the apex 119 of the left ventricle 123 is transected with a surgical tool to allow access to the interior of the ventricle. The device 111, comprising an expandable member 113 and an inflation tube 115, is inserted into the access incision and advanced into the ventricle 123 of the heart. Once the device 111 is properly positioned, either using tactile guidance, direct visualization, endoscopic visualization, fluoroscopic guidance or other well known visualization techniques, the expandable member 113 is expanded to reduce the ventricular volume of the heart. The appropriate degree of expansion as well as the proper placement and orientation may be clinically confirmed using the above visualization techniques. In one preferred technique, the expandable member 113 is a balloon configured from a radio-opaque or fluoroscopic material. Alternatively, the inflation fluid may be radio-opaque or fluoroscopically visible to allow ready visualization of the device 111 within the patient's ventricle 123.

Once the intra-ventricular volume displacement device 111 is in place within the ventricle, the access site is closed around the inflation tube 115 and the tube 115 is closed to prevent expansion/contraction of the expandable member 113. An end cap 117 may also be used to support the apex 119 of the left ventricle 123. Once in place, the inflation tube 115 may be left surgically accessible to allow additional adjustments as the clinical situation of the patient indicates. In one method, the inflation tube 115 may configured to remain outside the patient's body post-operatively so as to eliminate the need for future surgical access procedures on the patient. Alternatively, the tube 115 may be maintained subcutaneously so that a simple incision or puncture may be used post-operatively to adjust the expansion/contraction of the expandable member 113 within the ventricle 123. Aside from varying the location of the initial incision from the apex 119 of the ventricle 123 to the right ventricle 121, installation of the intra-ventricular volume displacement device 111 in the right ventricle 121 will vary little from the installation procedure for left ventricular volume reduction.

The intra-ventricular volume displacement device 111 may also be installed through the aorta of the patient (not shown) wherein the device is advanced through the aortic valve and into the left ventricle 123. In this configuration, the device 111 is fixed at the apex 111 of the ventricle 123 using sutures, staples, surgical adhesive, or other well known fastening techniques. Orientation and expansion of the device 111 is accomplished as discussed above. The inflation tube 115 may be considerably shorter or may be omitted entirely as the device 111 is maintained entirely intra-ventricularly in this configuration. For right heart assistance, the intra-ventricular volume displacement device 111 would be inserted via the pulmonary artery or the inferior or superior vena cava into the right atrium 129 and therethrough into the right ventricle 121 where it is installed as discussed above.

Figure 13:
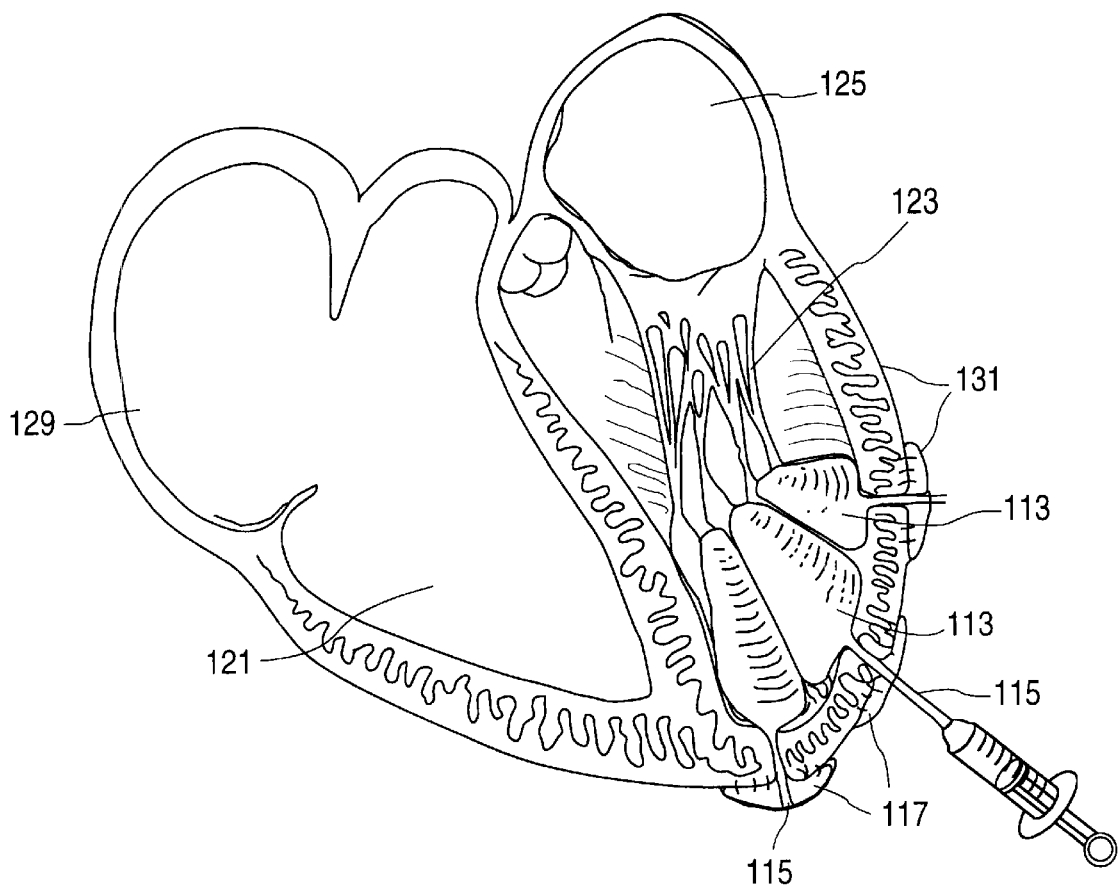
FIG. 13 is a cutaway view of the heart of the patient showing a plurality of intra-ventricular volume displacement devices installed within the apex of the ventricle.
Figure 14A:
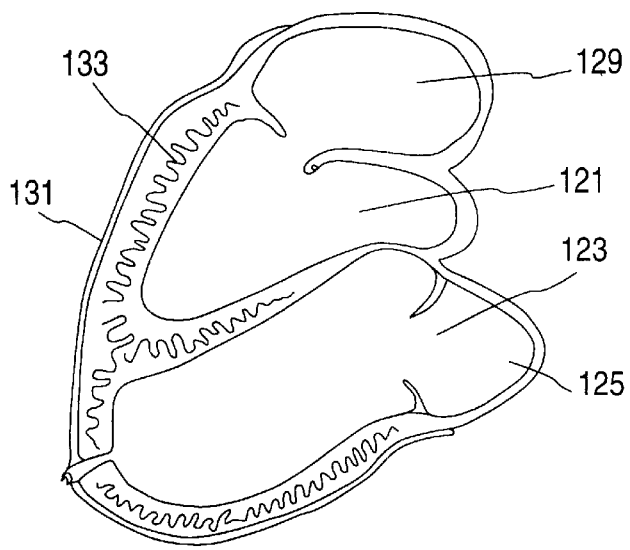
FIGS. 14(A–C) shows a method of reducing the ventricular volume of a enlarged heart wherein a portion of the pericardium is detached from the heart and is inserted into the ventricle to form a pericardial sack in the ventricle.
Figure 14B:
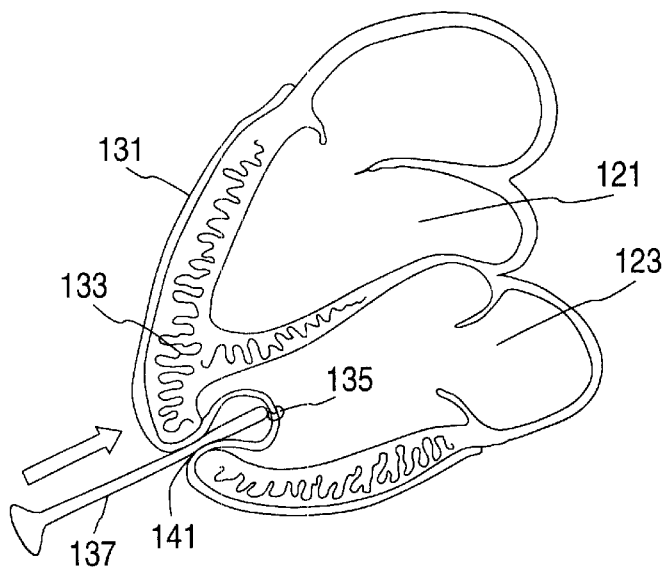
Figure 14C:
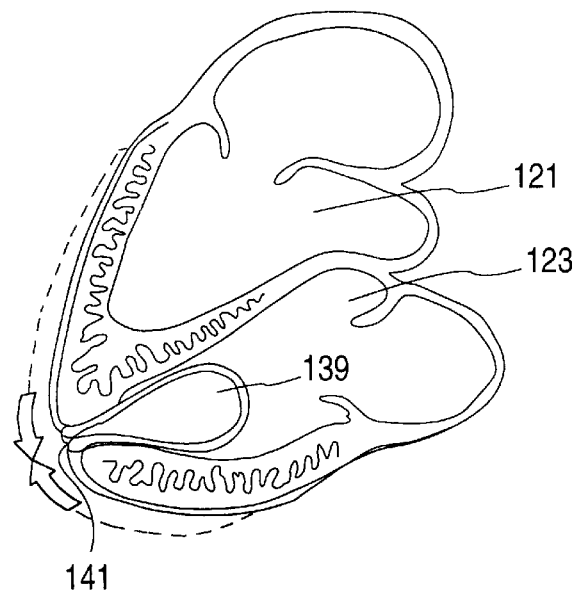

FIG. 13 shows another embodiment of an intra-ventricular volume displacement device 111 of the present invention suitable for reducing the ventricular volume of an hypertrophic heart comprising a plurality of expandable members 113 installed similarly to the procedure outlined above. The number and configuration of the expandable members 113 may be varied as the clinical situation indicates so as to maximize the pumping efficiency of the heart by controlling the internal volume and geometry of the ventricle 123. End caps 117 may be fixed to the myocardial surface 131 around the inflation tubes 115 so as to support the heart tissue and allow ready access to the inflation tubes 115. In addition to insertion of the devices using transmyocardial incisions, the devices 111 may also be installed via the aorta or the pulmonary artery, IVC or SVC to access the left 123 or right 121 ventricles.

The use of multiple expandable members 111 allows the surgeon to custom fit the ventricular volume reduction as the clinical situation indicates. In a preferred method, a first intra-ventricular volume displacement device is installed in a beating heart and the surgeon assesses the degree of improvement in cardiac performance. If the clinical situation indicates, a second intra-ventricular volume displacement device is installed. This process is repeated until the clinical situation indicates maximum efficiency from the beating heart. A volume displacement device may also be configured to displace a portion of the blood volume of the right or left atrium.

FIGS. 13(A–C) show another method of the present invention for treating a hypertrophic heart. In FIG. 13A, the pericardium 131 and myocardium 133 at the apex 119 of the left ventricle 123 are transected surgically to access the ventricle 123 of the patient. The surgeon then repairs the pericardial incision 135 and the pericardium 131 is pushed into the ventricle using a surgical instrument 137 or other tool (i.e. the surgeon's finger) to form a pericardial sack 139 disposed within the ventricle 123 of the patient as shown in FIGS. 13(B–C). Care must be taken to avoid tearing the pericardial incision 135 when pushing the tissue into the ventricle 123. Once the pericardium is adequately inserted into the ventricle, it is filled with saline solution or other suitable biocompatible material and then the mouth 141 of the pericardial sack 139 is sutured shut to prevent escape of the inflation fluid.

In an alternative configuration (not shown), a surgical instrument may be inserted into the left ventricle of the heart via the left atrium. The instrument is used to incise only the myocardium 133 of the patient and leave the pericardium 131 intact. The remainder of the procedure is unchanged from that discussed above. Leaving the pericardium 131 intact ensures the patency of the pericardial sack 135 that is formed within the ventricle 123 of the patient and prevents loss of inflation fluid postoperatively. For reducing the right ventricular volume of the heart, the access location is varied from the apex 119 of the left ventricle 123 but the remainder of the method is generally unchanged from left heart ventricular volume reduction. The above methods may also be practiced to reduce the atrial volume of the right 129 and left 125 atria if the clinical situation so indicates.

The particular examples set forth herein are instructional and should not be interpreted as limitations on the applications to which those of ordinary skill are able to apply this invention. Modifications and other uses are available to those skilled in the art which are encompassed within the spirit and scope of the following claims.

We claim:

1. A method of passively increasing the cardiac output of a heart by restraining a portion of the heart, the method comprising the steps of:
   a) providing a site of surgical access to a portion of the heart to be restrained;
   b) reducing the cardiac expansion of the portion of the heart to be restrained;
   c) wherein the step of reducing the cardiac expansion of the portion of the heart to be restrained comprises applying a ventricular assist device to the surface of the heart, the ventricular assit device comprising a frame having at least one lateral support member connected to at least one vertical support member and a net attached to the frame, the frame and net being configured to surround the portion of the heart to be restrained; and
   d) maintaing the reduction of cardiac expansion of the portion of the heart to be restrained postoperatively.

2. The method of claim 1 wherein the ventricular assist device further comprises a retaining strap attached to the frame.

3. The method of claim 2, wherein the retaining strap has two ends, and further comprising the step of attaching the ventricular assist device to the heart by inserting the retaining strap through the heart and attaching each end of the retaining strap to the frame of the ventricular device.

4. The method of claim 1, further comprising the step of bending the frame to place pressure on a specific area of the portion of the heart to be restrained.

5. The method of claim 1, further comprising the step of bending the net to place pressure on a specific area of the portion of the heart to be restrained.

6. The method of claim 1, wherein the frame and net are made of biocompatible material.

7. The method of claim 6, wherein the biocompatible material is a relatively flexible material.

8. The method of claim 6, wherein the biocompatible material is a relatively rigid material.

9. The method of claim 1 including the additional step of assessing the degree of cardiac assistance achieved from the reduction of cardiac expansion in the portion of the heart to be restrained.

10. The method of claim 1 further including the step of placing the patient on cardiopulmonary bypass prior to reducing the cardiac expansion of the portion of the heart to be restrained.

11. The method of claim 1 wherein the method is performed in a minimally invasive manner.

12. The method of claim 1 wherein the method is performed on a beating heart.

* * * * *